(12) United States Patent
Wang

(10) Patent No.: US 11,203,582 B2
(45) Date of Patent: Dec. 21, 2021

(54) BENZAMIDE DERIVATIVES FOR INHIBITING ENDOPLASMIC RETICULUM (ER) STRESS

(71) Applicant: The Board of Regents of the University of Oklahoma, Norman, OK (US)

(72) Inventor: Weidong Wang, Edmond, OK (US)

(73) Assignee: The Board of Regents of the University of Oklahoma, Norman, OK (US)

( * ) Notice: Subject to any disclaimer, the term of this patent is extended or adjusted under 35 U.S.C. 154(b) by 0 days.

(21) Appl. No.: 16/621,154

(22) PCT Filed: Jun. 15, 2018

(86) PCT No.: PCT/US2018/037790
§ 371 (c)(1),
(2) Date: Dec. 10, 2019

(87) PCT Pub. No.: WO2018/232264
PCT Pub. Date: Dec. 20, 2018

(65) Prior Publication Data
US 2020/0199094 A1 Jun. 25, 2020

Related U.S. Application Data

(60) Provisional application No. 62/520,019, filed on Jun. 15, 2017.

(51) Int. Cl.
| | |
|---|---|
| *C07D 319/18* | (2006.01) |
| *C07C 233/65* | (2006.01) |
| *C07D 207/09* | (2006.01) |
| *C07D 211/34* | (2006.01) |
| *C07D 317/68* | (2006.01) |

(52) U.S. Cl.
CPC .......... *C07D 319/18* (2013.01); *C07C 233/65* (2013.01); *C07D 207/09* (2013.01); *C07D 211/34* (2013.01); *C07D 317/68* (2013.01)

(58) Field of Classification Search
CPC .. C07D 319/18; C07D 207/09; C07D 211/34; C07D 317/68; C07C 233/65
See application file for complete search history.

(56) References Cited

U.S. PATENT DOCUMENTS

| | | | | |
|---|---|---|---|---|
| 7,238,688 | B2* | 7/2007 | Rosenblum .......... | C07D 211/26 514/217.05 |
| 8,809,538 | B2 | 8/2014 | Rodriguez et al. | |
| 10,815,219 | B2* | 10/2020 | Wang .................... | A61K 47/51 |
| 2006/0167044 | A1 | 7/2006 | Arnaiz et al. | |
| 2007/0142369 | A1* | 6/2007 | van Heek .............. | A61P 3/10 514/227.5 |
| 2009/0036420 | A1 | 2/2009 | Galley et al. | |
| 2010/0234424 | A1 | 9/2010 | Dargazanli et al. | |
| 2019/0047988 | A1* | 2/2019 | Wang .................... | C07D 403/04 |
| 2019/0322662 | A1* | 10/2019 | Lindsley ............... | C07D 271/10 |
| 2020/0071264 | A1* | 3/2020 | Wang .................... | C07C 233/73 |

OTHER PUBLICATIONS

Chemical Abstracts, STN Registry Database, Record for RN 1048313-20-7, "3-[[4-(phenylmethyl)-1-piperidinyl]methyl]-N-[[3-(trifluoromethyl)phenyl]methyl]benzamide", entered into STN on Sep. 10, 2008. (Year: 2008).*
Eeda; Chem Biol Drug Des. 2020, 95, 388-393. (Year: 2020).*
National Center for Biotechnology Information. "PubChem Compound Summary for CID 71178128" PubChem, https://pubchem.ncbi.nlm.nih.gov/compound/71178128. Accessed Oct. 16, 2020. Create Date Mar. 21, 2013. (Year: 2013).*
National Center for Biotechnology Information. PubChem Substance Record for SID 96605905, SID 96605905, Source: DiscoveryGate. https://pubchem.ncbi.nlm.nih.gov/substance/96605905. Date Available May 24, 2010. (Year: 2010).*
Chemical Abstracts STN Registry Database, record for RN 1170190-09-6, Entered into STN on Jul. 29, 2009. (Year: 2009).*
Schuit, F.C., et al.; "Glucose stimulates proinsulin biosynthesis by a dose-dependent recruitment of pancreatic beta cells"; Proc. Natl. Acad. Sci. USA 85 (1988) 3865-3869.
Slee, E.A., et al.; "Ordering the Cytochrome c-initiated Caspase Cascade: Hierarchical Activation of Caspases-2, -3, -6, -7, -8, and -10 in a Caspage-9-dependent Manner"; The Journal of Cell Biology 144:2 (1999) 281-292.
Bertolotti, A., et al.; "Dynamic interaction of BiP and ER stress transducers in the unfolded-protein response"; Nature Cell Biology 2 (2000) 326-332.
Herceg, Z., et al.; "Functions of poly(ADP-ribose) polymerase (PARP) in DNA repair, genomic integrity and cell death"; Mutation Research 477 (2001) 97-110.
Kataoka, K., et al.; "MafA Is a Glucose-regulated and Pancreatic B-Cell-specific Transcriptional Activator for the Insulin Gene"; The Journal of Biological Chemistry 244:51 (2002) 49903-49910.
Donath, M.Y., et al.; "Decreased beta-cell mass in diabetes: significance, mechanisms and therapeutic implications"; Diabetology 47 (2004) 581-589.
Schroder, M., et al.; "ER stress and the unfolded protein response"; Mutation Research 569 (2005) 29-63.
Prentki, M., et al.; "Islet B cell failure in type 2 diabetes"; J Clin Invest. 116:7 (2006) 1802-1812.
Van Lommel, L., et al.; "Probe-Independent and Direct Quantification of Insulin mRNA and Growth Hormone mRNA in Enriched Cell Preparations"; Diabetes 55 (2006) 3214-3220.

(Continued)

*Primary Examiner* — Daniel R Carcanague
(74) *Attorney, Agent, or Firm* — Hall Estill Law Firm

(57) ABSTRACT

Novel 3-(N-piperidinyl)methyl benzamide derivatives are disclosed. The compounds can be used in treating diseases and conditions which are associated with abnormal cell function related to endoplasmic reticulum (ER) stress. For example, the compounds can be used as suppressors of ER stress-induced pancreatic β-cell dysfunction and death, for example in the treatment of diabetes.

27 Claims, 9 Drawing Sheets
(4 of 9 Drawing Sheet(s) Filed in Color)
Specification includes a Sequence Listing.

(56) References Cited

OTHER PUBLICATIONS

Cnop, M., et al.; "Selective Inhibition of Eukaryotic Translation Initiation Factor 2a Dephosphorylation Potentiates Fatty Acid-induced Endoplasmic Reticulum Stress and Causes Pancreatic B-Cell Dysfunction and Apoptosis"; The Journal of Biological Chemistry 282:6 (2007) 3989-3997.
Eizirik, D.L., et al.; "The Rose for Endoplasmic Reticulum Stress in Diabetes Mellitus"; Endocrine Reviews 29:1 (2008)42-61.
Scheuner, D., et al.; "The Unfolded Protein Response: A Pathway That Links Insulin Demand with B-Cell Failure and Diabetes"; Endocrine Review 29:3 (2008) 317-333.
Ladriere, L., et al.; "Enhanced Signaling Downstream of Ribonucleic Acid-Activated Protein Kinase-Like Endoplasmic Reticulum Kinase Potentiates Lipotoxic Endoplasmic Reticulum Stress in Human Islets"; J Clin Endocrinol Metab 95:3 (2010) 1442-1449.
Fonseca, S.G., et al.; "Endoplasmic reticulum stress and pancreatic B-cell death"; Trends in Endocrinology and Metabolism 22:7 (2011) 266-274.
Tabas, I., et al.; "Integrating the mechanisms of apoptosis induced by endoplasmic reticulum stress"; Nature Cell Biology 13:3 (2011) 184-190.
Walter, P., et al.; "The Unfolded Protein Response: From Stress Pathway to Homeostatic Regulation"; Science 334 (2011) 1081-1086.
Zhang, R., et al.; "Protective Mechanism of KIOM-4 in Streptozotocin-Induced Pancreatic B-Cells Damage Is Involved in the Inhibition of Endoplasmic Reticulum Stress"; Evidence-Based Complementary and Alternative Medicine 2011:ID231938 (2011) 10 pages.
Back, S.H., et al.; "Endoplasmic Reticulum Stress and Type 2 Diabetes"; Annu. Rev. Biochem. 81 (2012) 767-793.
Tersey, S.A., et al.; "Islet B-Cell Endoplasmic Reticulum Stress Precedes the Onset of Type 1 Diabetes in the Nonobese Diabetic Mouse Model"; Diabetes 61 (2012) 818-827.
Papa, F.R.; "Endoplasmic Reticulum Stress, Pancreatic B-Cell Degeneration, and Diabetes"; Cold Spring Harb Perspect Med (2012) 18 pages.
Wang, S., et al.; "The impact of the unfolded protein response on human disease"; J. Cell Biol. 197:7 (2012) 857-867.
Engin, F., et al.; "Restoration of the Unfolded Protein Response in Pancreatic B Cells Protects Mice Against Type 1 Diabetes"; www.ScienceTranslationalMedicine.org 5:211 (2013) 16 pages.
Hetz, C., et al.; "Targeting the unfolded protein response in disease"; Nature Reviews—Drug Discovery 12 (2013) 703-719.
Tran, K., et al.; "Identification of Small Molecules That Protect Pancreatic B Cells against Endoplasmic Reticulum Stress-Induced Cell Death"; ACS Chem Biol. 9 (2014) 2796-2806.
Vetere, A., et al.; "Targeting the pancreatic B-cell to treat diabetes"; www.nature.com/reviews/drugdisc 13 (2014) 278-289.
Ahn, C., et al.; "Streptozotocin induces endoplasmic reticulum stress and apoptosis via disruption of calcium homeostatis in mouse pancreas"; Molecular and Cellular Endocrinology 412 (2015) 302-308.
Rutter, G., et al.; "Pancreatic B-cell identity, glucose sensing and the control of insulin secretion"; Biochem. J. 466 (2015) 203-218.
Senft, D., et al.; "UPR, autophagy, and mitochondria crosstalk underlies the ER stress response"; Trends in Biochemical Sciences 40:3 (2015) 141-148.
Duan, H., et al.; "Discovery, Synthesis, and Evaluation of 2,4-Diaminoquinazolines as a Novel Class of Pancreatic B-Cell-Protective Agents against Endoplasmic Reticulum (ER) Stress"; J. Med. Chem. 59 (2016) 7783-7800.
Duan, H., et al.; "Discovery of a benzamide derivative that protects pancreatic B-cells against endoplasmic reticulum stress"; J. Med. Chem. 60:14 (2017) 6191-6204.
PCT/US2018/037790; "International Search Report and Written Opinion"; International Searching Authority; dated Sep. 14, 2018; 10 pages.

\* cited by examiner

Scheme 1

Scheme 2

Scheme 3

SEQUENCE LISTING

```
<160> NUMBER OF SEQ ID NOS: 22

<210> SEQ ID NO 1
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 1
gaaatcgagc gcctgaccag                                              20

<210> SEQ ID NO 2
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 2
ggaggtgatg ccaacagttc a                                            21

<210> SEQ ID NO 3
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 3
tcctgaacag cgaagtgttg                                              20

<210> SEQ ID NO 4
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 4
gtgtctgagg cactgaccaa                                              20

<210> SEQ ID NO 5
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 5
ctattcctgc gtcggtgtat t                                            21

<210> SEQ ID NO 6
<211> LENGTH: 21
<212> TYPE: DNA
```

```
<213> ORGANISM: Artificial Sequence
<220> FEATURE:
<223> OTHER INFORMATION: Completely synthesized in the lab.

<400> SEQUENCE: 6
ggttggacgt gagttggttc t                                            21

<210> SEQ ID NO 7
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 7
tcccccttaa tgtttcccgt g                                            21

<210> SEQ ID NO 8
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 8
tagcccttct tcagaagcct c                                            21

<210> SEQ ID NO 9
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 9
ctgagtccga atcaggtgca g                                            21

<210> SEQ ID NO 10
<211> LENGTH: 21
<212> TYPE: DNA
<213> ORGANISM: Artificial Sequence
<220> FEATURE:
<223> OTHER INFORMATION: Completely synthesized in the lab.

<400> SEQUENCE: 10
atccatggga agatgttctg g                                            21

<210> SEQ ID NO 11
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 11
gcttgtgatt gagaaccagg                                              20

<210> SEQ ID NO 12
<211> LENGTH: 22
<212> TYPE: DNA
<213> ORGANISM: Artificial Sequence
<220> FEATURE:
<223> OTHER INFORMATION: Completely synthesized in the lab.

<400> SEQUENCE: 12
gaaagggagg ctggtaagga ac                                           22
```

<210> SEQ ID NO 13
<211> LENGTH: 18
<212> TYPE: DNA
<213> ORGANISM: Artificial Sequence
<220> FEATURE:
<223> OTHER INFORMATION: Completely synthesized in the lab.

<400> SEQUENCE: 13
gtcctctggg agcccaag                                                 18

<210> SEQ ID NO 14
<211> LENGTH: 17
<212> TYPE: DNA
<213> ORGANISM: Artificial Sequence
<220> FEATURE:
<223> OTHER INFORMATION: Completely synthesized in the lab.

<400> SEQUENCE: 14
acagagcctc caccagg                                                  17

<210> SEQ ID NO 15
<211> LENGTH: 18
<212> TYPE: DNA
<213> ORGANISM: Artificial Sequence
<220> FEATURE:
<223> OTHER INFORMATION: Completely synthesized in the lab.

<400> SEQUENCE: 15
atcctctggg agccccgc                                                 18

<210> SEQ ID NO 16
<211> LENGTH: 17
<212> TYPE: DNA
<213> ORGANISM: Artificial Sequence
<220> FEATURE:
<223> OTHER INFORMATION: Completely synthesized in the lab.

<400> SEQUENCE: 16
agagagcttc caccaag                                                  17

<210> SEQ ID NO 17
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 17
gaggacccgt acagcctaca                                               20

<210> SEQ ID NO 18
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 18
cgttgtcccg ctactacgtt                                               20

<210> SEQ ID NO 19
<211> LENGTH: 20
<212> TYPE: DNA
<213> ORGANISM: Artificial Sequence
<220> FEATURE:

```
<223> OTHER INFORMATION: Completely synthesized in the lab.

<400> SEQUENCE: 19
agcggtcata ttttcgcaac                                              20

<210> SEQ ID NO 20
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 20
ctctacaggg agcagcgaac                                              20

<210> SEQ ID NO 21
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 21
ggtgacttca cacgccataa                                              20

<210> SEQ ID NO 22
<211> LENGTH: 20
<212> TYPE: DNA
<213> ORGANISM: Artificial Sequence
<220> FEATURE:
<223> OTHER INFORMATION: Completely synthesized in the lab.

<400> SEQUENCE: 22
cttcccaaag accacatgct                                              20
```

BENZAMIDE DERIVATIVES FOR INHIBITING ENDOPLASMIC RETICULUM (ER) STRESS

CROSS-REFERENCE TO RELATED APPLICATIONS

The present application is a national stage application of a PCT application having International Application No. PCT/US2018/037790, filed Jun. 15, 2018, which claims priority to U.S. Provisional Application having U.S. Ser. No. 62/520,019, filed Jun. 15, 2017, which claims the benefit under 35 U.S.C. 119(e), the disclosure of which is hereby expressly incorporated herein by reference.

GOVERNMENT SUPPORT

This invention was made with government support under Contract Number GM103636 and DK108887 awarded by the National Institutes of Health (NIH). The government has certain rights in the invention.

BACKGROUND

Diabetes, a group of metabolic diseases in which blood sugar levels are abnormally high over a prolonged period, has become a serious public health problem with tremendous social and economic burden on society. As of 2015, 415 million people worldwide were estimated to suffer from have diabetes. The dysfunction and death of insulin-producing pancreatic β-cells are critical elements in the pathogenesis of type 1 (T1D) and type 2 (T2D) diabetes. Increasing evidence indicates that endoplasmic reticulum (ER) stress, a condition in which misfolded proteins accumulate in the ER, plays an important role in the decline in pancreatic β-cell function and mass in diabetes. Thus, prevention of functional pancreatic β-cell death by mitigating ER stress is a promising therapeutic approach for patients with diabetes. Unfortunately, no existing anti-diabetic drugs have been known that are capable of halting the progression of β-cell dysfunction and death.

In T2D, β-cells are forced to synthesize more insulin due to higher metabolic demands of obesity and insulin resistance, which typically exceeds the cellular capacity of the ER for protein folding, and eventually leads to ER stress and β-cell dysfunction and death. In addition, the common causes for β-cell dysfunction and death in T2D, including lipotoxicity, glucotoxicity, oxidative stress, amyloid deposition, and insulin mutations, have been known to be associated with unresolvable chronic ER stress. In T1D in which β-cells are destroyed by an auto-immune reaction, ER stress has also been implicated, and an ER stress-reducing chemical chaperone has been reported to prevent the onset of T1D in mouse models by protecting β-cell survival.

ER stress induces activation of the unfolded protein response (UPR) through three ER membrane proteins, inositol-requiring protein 1αα(IRE1α), PKR-like ER kinase (PERK), and activating transcription factor 6 (ATF6), which act as unfolded protein sensors. In unstressed cells, these sensors are maintained in an inactive state through interaction with the protein chaperone binding immunoglobulin protein (BiP). Under ER stress, unfolded and misfolded proteins accumulate in the ER and bind to and sequester BiP, thereby releasing and activating the sensors. Upon initial or mild ER stress, IRE1α, PERK, and ATF6 each activate a series of events aimed at restoring ER homeostasis by altering the translation, folding, and post-translational modification of secreted and membrane proteins. However, failure to adequately re-establish ER homeostasis eventually triggers cell death, as in the case of chronic or severe ER stress.

Despite the importance of ER stress in mediating β-cell dysfunction and death in the pathogenesis of diabetes, only a handful of small molecules have so far been reported to exhibit β-cell-protective activities against ER stress. A major reason for the scarcity of β-cell-protective small molecules could lie in the unique property of β-cells. β-cells normally produce and rapidly secrete insulin in response to increases in blood glucose levels after food intake. To achieve this, they maintain a very large pool of proinsulin mRNA (~20% of the total cellular mRNA) and increase proinsulin protein synthesis 25-fold upon glucose stimulation. This surge in proinsulin synthesis places a heavy burden on the protein-folding capacity of the ER; β-cells are therefore particularly susceptible to ER stress. This β-cell property may also in part explain why compounds that protect other cell types from ER stress fail to protect β-cells. Furthermore, the existing β-cell-protective small molecules still suffer from the issue of low potency, often with $EC_{50}$ values ranging from single- to double-digit μM. New high potency small molecules for protecting pancreatic β-cell mass are thus greatly desired.

BRIEF DESCRIPTION OF THE DRAWINGS

Several embodiments of the present disclosure are hereby illustrated in the appended drawings. It is to be noted however, that the appended drawings only illustrate several embodiments and are therefore not intended to be considered limiting of the scope of the present disclosure. The patent or application file contains at least one drawing executed in color. Copies of this patent or patent application publication with color drawing(s) will be provided by the Office upon request and payment of the necessary fee.

Results in all panels are the means of 3 replicate wells and are representative of 3 independent experiments. Error bars indicate standard deviation (SD). * P<0.05,  P<0.01, and * P<0.001 compared with Tm treated alone.

Figure 3:
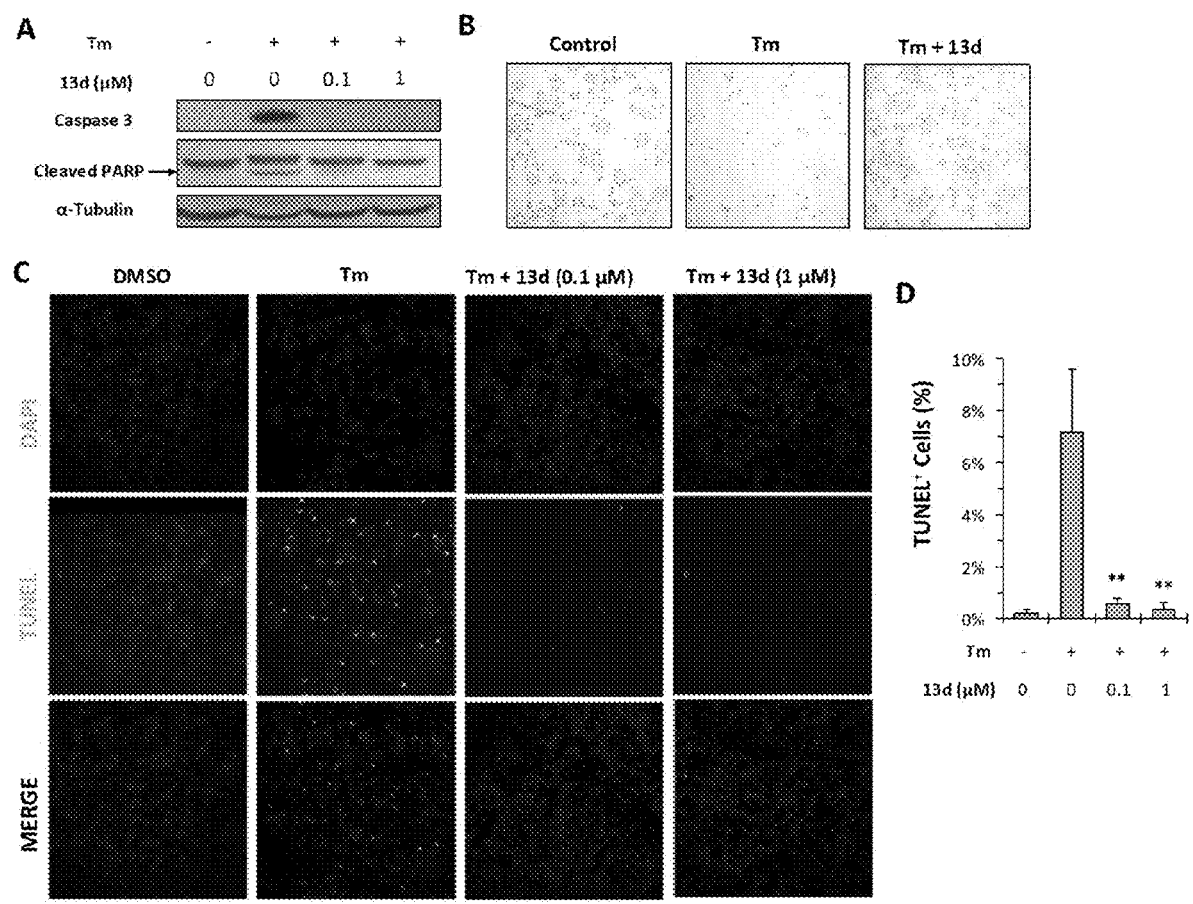

FIG. 3 shows that compound 13d protects INS-1 cells against Tm-induced apoptosis. (A) INS-1 cells were treated with or without Tm (0.1 m/mL) in the presence of 13d at indicated concentrations or DMSO for 24 h. Cleaved caspase-3 and PARP were determined by Western blotting. α-Tubulin was used as a loading control. The data shown are representative of 3 independent experiments. (B) INS-1 cells were treated with or without Tm (0.1 m/mL) in the presence of 13d (0.1₁1M) or DMSO for 48 h, and live-cell phase-contrast images were acquired (magnification 10×). The images shown are representative of 3 independent experiments. (C) TUNEL staining of INS-1 cells. INS-1 cells were treated with 0.1₁1 g/mL of Tm with or without compound 13d for 24 h before TUNEL staining. DAPI was used as a nuclear marker. Magnification is 20×. The images shown are representative of 3 independent experiments. (D) Quantification of TUNEL staining from 20 fields of images. ** P<0.01 compared with Tm treatment alone.

Figure 4:
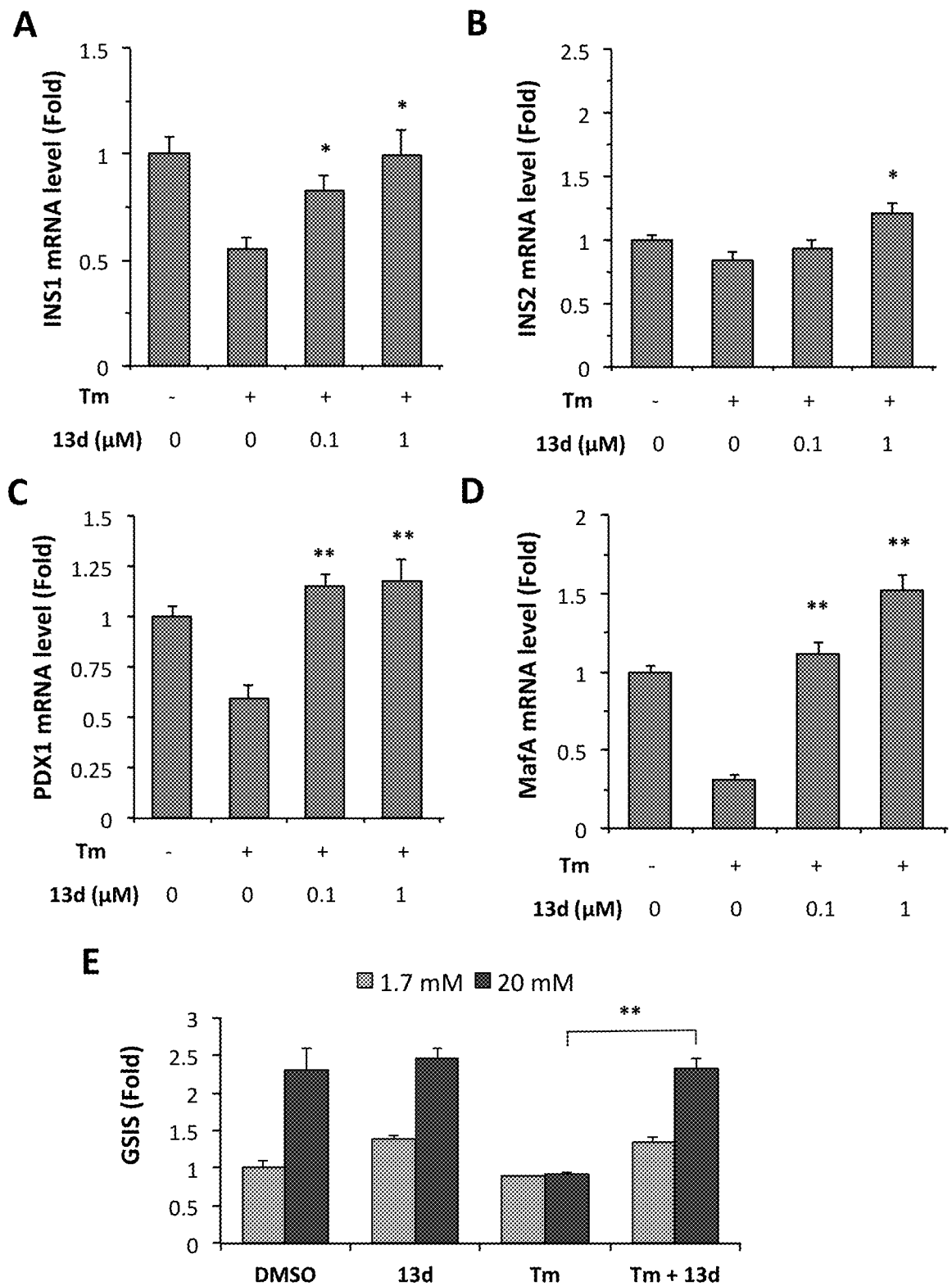

FIG. 4 shows that compound 13d reversed Tm-suppressed β-cell dysfunction. (A-D) INS-1 cells were treated with or without Tm (0.1 m/mL) in the presence of 13d at indicated concentrations or DMSO for 24 h. The mRNA levels of INS1 (A), INS2 (B), PDX1 (C), and MafA (D), were analyzed by qRT-PCR. Relative mRNA levels were normalized against the housekeeping gene Cyclophilin A using the comparative CT method. The results are the means of 3 replicate wells and are representative of 3 independent experiments. * P<0.05 and ** P<0.01 compared with Tm treatment alone. Bars indicate SD. (E) Insulin secretion by INS-1 cells incubated with 1.7 mM and 20 mM glucose in the presence or absence of Tm (0.1 μg/mL) and 13d. Secreted insulin was measured by ELISA after 24 h treatment. * P<0.05. The amount of insulin secreted in response to 1.7 mM glucose in the absence of Tm was set to 1.0 and was normalized with total protein concentration.

Figure 5:
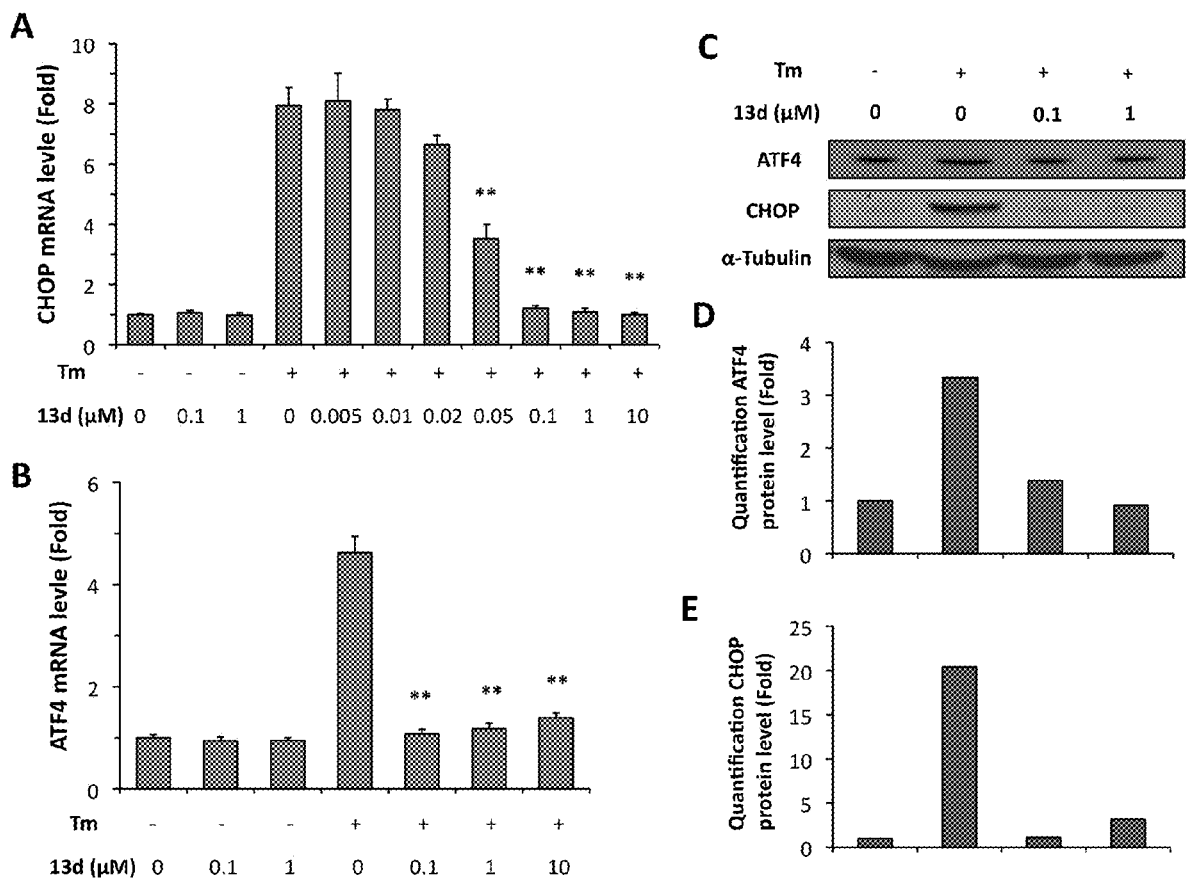

FIG. 5 shows that compound 13d inhibits Tm-induced ATF4 and CHOP up-regulation in INS-1 cells. (A, B) INS-1 cells were treated with or without Tm (0.1 μg/mL) in the presence of 13d or DMSO for 8 h. ATF4 (A) and CHOP (B) mRNA levels were analyzed by qRT-PCR. Relative mRNA levels were normalized against the housekeeping gene Cyclophilin A using the comparative CT method. The results were expressed as the fold-increase over mRNA levels in untreated control cells and are the means of 3 replicate wells and representative of 3 independent experiments. ** P<0.01 compared with Tm treatment alone. Bar indicates SD. (C-E) INS-1 cells were treated with or without Tm (0.1 μg/mL) in the presence of 13d or DMSO for 8 hATF4 and CHOP protein levels were determined by Western blotting (C). α-Tubulin was used as an internal control. Quantification of ATF4 (D) and CHOP (E) protein levels was analyzed by ImageJ program, which was normalized by α-Tubulin protein level. The data shown are representative of 3 independent experiments.

Figure 6:
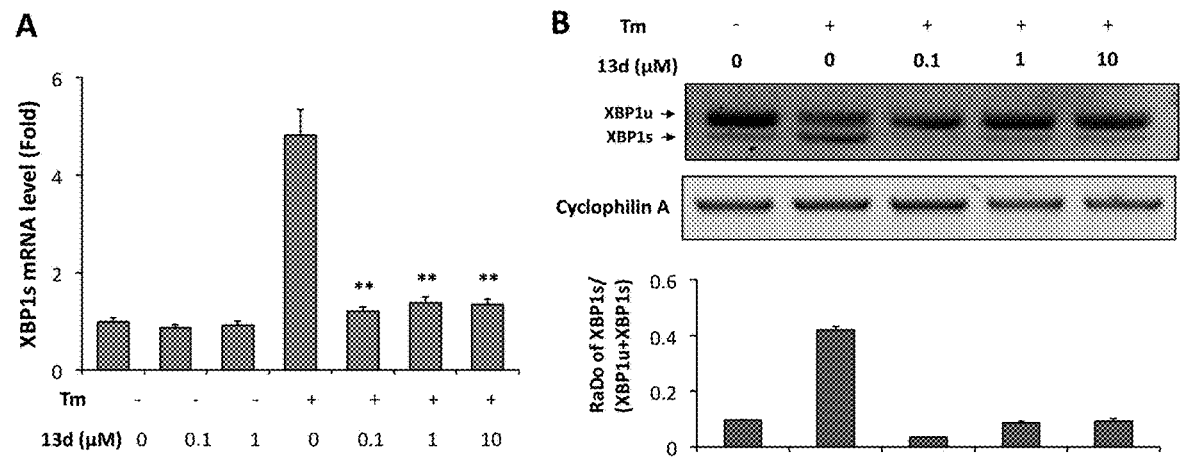

FIG. 6 shows compound 13d inhibits Tm-induced XBP1s mRNA expression in INS-1 cells. INS-1 cells were treated with or without Tm (0.1 μg/mL) in the presence of 13d or DMSO for 8 h. (A) XBP1s mRNA levels were analyzed by qRT-PCR. Relative mRNA levels were normalized against the housekeeping gene Cyclophilin A using the comparative CT method. ** P<0.01 compared with Tm treatment alone. Bars indicate SD. (B) XBP1 mRNA levels were analyzed by RT-PCR and the products were resolved by agarose gel electrophoresis. The full-length (unspliced, XBP1u) and spliced (XBP1s) forms of XBP1 mRNA are indicated. Cyclophilin A mRNA was used as a loading control. Quantification was analyzed by ImageJ program shown at the bottom. The data shown are representative of 3 independent experiments.

Figure 7:
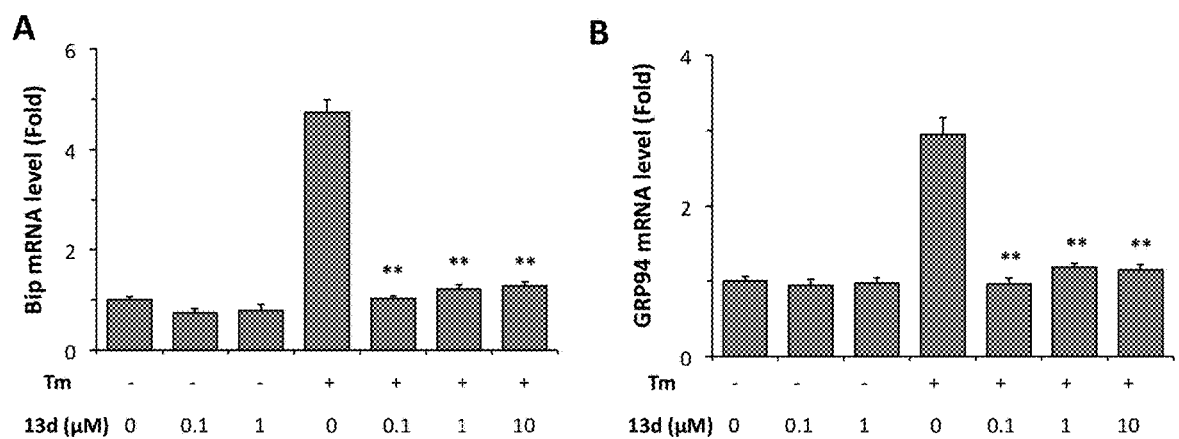

FIG. 7 shows that compound 13d decreases Bip and GRP94 mRNA levels induced by Tm. INS-1 cells were treated with or without Tm (0.1 μg/mL) in the presence of 13d or DMSO for 8 h. Bip (A) and GRP94 (B) mRNA levels were analyzed by qRT-PCR. Relative mRNA levels were normalized against the housekeeping gene Cyclophilin A using the comparative CT method. The results are the means of 3 replicate wells and representative of 3 independent experiments. ** P<0.01 compared with Tm treatment alone. Error bars indicate SD.

Figure 8:
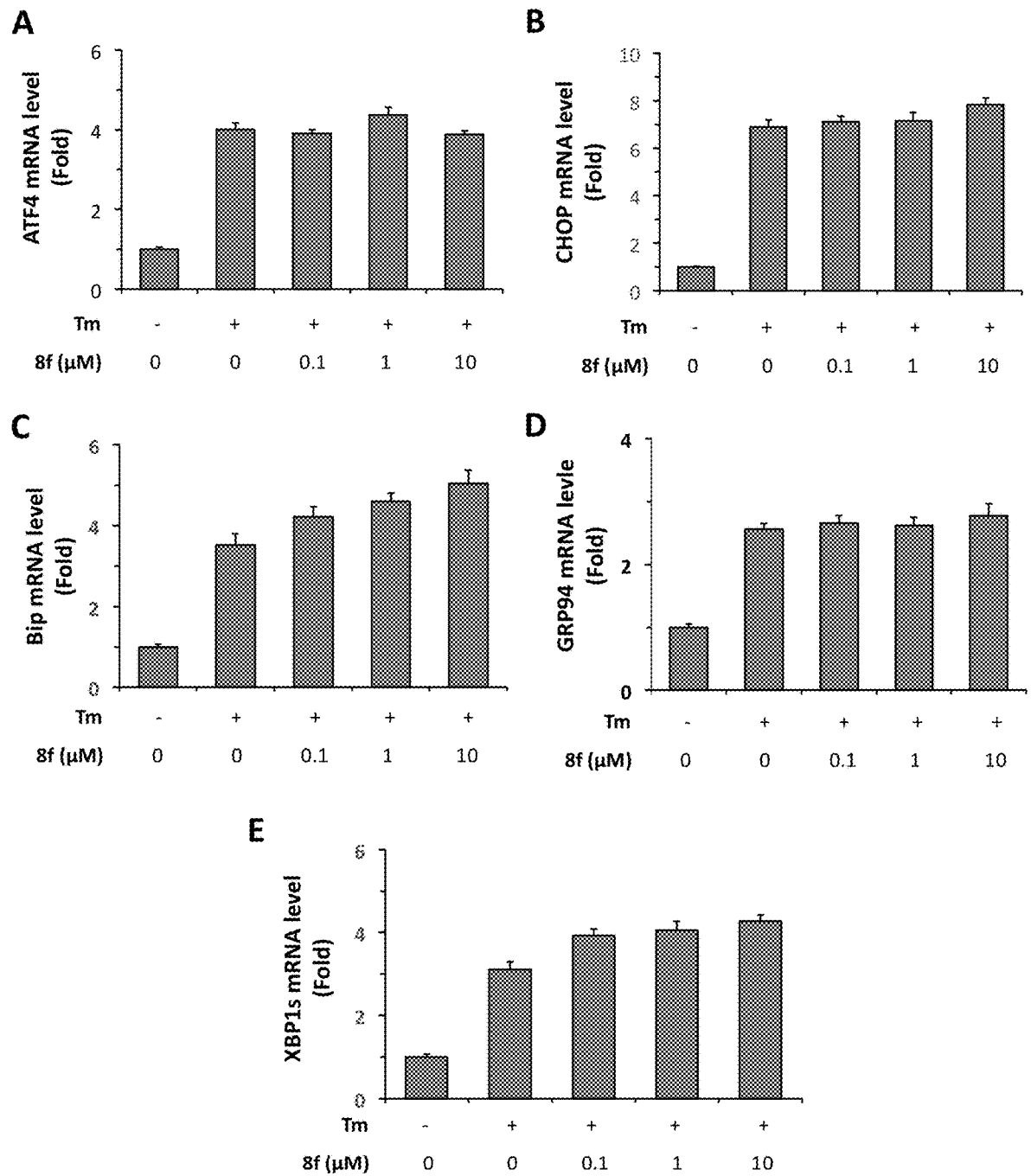

FIG. 8 shows that inactive compound 8f does not decrease ER stress related mRNA levels induced by Tm. INS-1 cells were treated with or without Tm (0.1 m/mL) in the presence of 8f or DMSO for 8 h. ATF4 (A), CHOP (B), Bip (C), GRP94 (D), and XBP1s (E) mRNA levels were analyzed by qRT-PCR. Relative mRNA levels were normalized against the housekeeping gene Cyclophilin A using the comparative CT method. The results are the means of 3 replicate wells and representative of 3 independent experiments. Error bars indicate SD.

Figure 9:
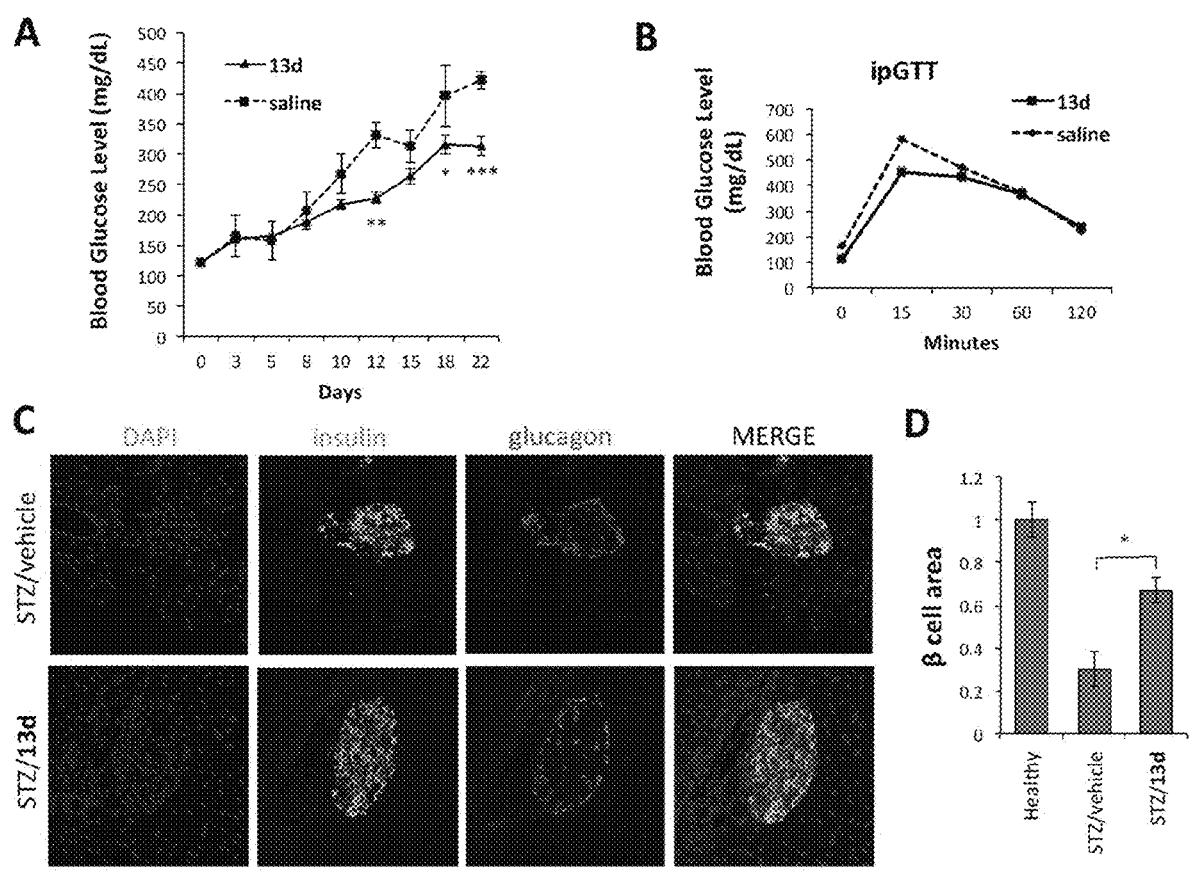

FIG. 9 shows an anti-diabetic effect of 13d in the STZ-induced diabetic mouse model. (A) Fasting blood glucose levels were measured in STZ-injected mice treated with vehicle control (n=6) or 13d (n=7). C57BL/6J mice were injected intraperitoneally once daily for 5 days with STZ (50 mg/kg body weight) and with either vehicle (n=6 mice) or 13d (5 mg/kg body weight; n=7 mice). Injections of vehicle or 13d alone were then continued for 2 more weeks. (B) Glucose tolerance test. Blood glucose levels measured at indicated time points after intraperitoneal injection of glucose (2 g/kg body weight). (C) Pancreases were sectioned and slides were stained with anti-insulin antibody (green, β-cell marker), anti-glucagon antibody (red, α-cell marker), and DAPI (blue). Slides were imaged with an Olympus FV1000 confocal microscope. Representative images are shown in (C). (D) Quantification of total islet area per section and β-cell number per islet. Total area of all islets per section calculated for a total of six sections using insulin-positive cells to demarcate islets. Data are the means±SEM of six sections from three mice. *p<0.05 p<0.01, and *p<0.001 by Student's t-test.

Figure 10:
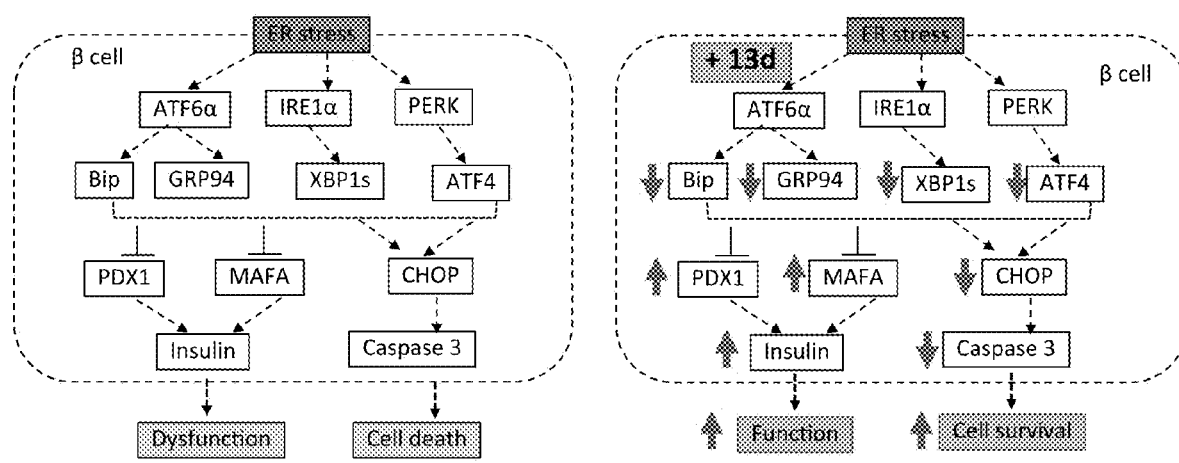

FIG. 10 shows a proposed model of signaling pathways involved in 13d-mediated β-cell-protective effects against ER stress. ER stress induces activation of three branches of UPR (ATF6, IRE1α, and PERK), leading to up-regulation of Bip, GRP4, XBP1s, ATF4, and CHOP. These events result in the reduction in the expression of PDX1, MAFA and insulin genes, leading to β-cell dysfunction, and the eventual activation of caspase 3 and cell apoptosis. In the model, compound 13d protects β-cells against ER stress-mediated dysfunction and death by attenuating ER stress through down-regulating ATF4, XBP1s, Bip, GRP94, CHOP, and caspase 3, and up-regulating PDX1, MAFA and insulin genes.

DETAILED DESCRIPTION

The present disclosure is directed to novel (N-piperidinyl) methyl benzamide derivatives, particularly 3-(N-piperidinyl) methyl benzamide derivatives. The compounds are effective in inhibiting ER stress. For example, the compounds can be used as potent suppressors of ER stress-induced β-cell death and dysfunction. In at least one non-limiting embodiment, the derivative compound N-(4-trifluoromethylphenmethyl)-3-(N-piperidinyl)methyl benzamide has near 100% β-cell-protective activity and an $EC_{50}$ of 0.032 µM against ER stress, and significantly lowers blood glucose levels and increases β-cell survival in an STZ-induced diabetic mouse model. Further, the compound alleviates ER stress/UPR response by inhibiting Tm-induced up-regulation of all three branches of unfolded protein response (UPR) and apoptosis.

Before further describing various embodiments of the present disclosure in more detail by way of exemplary description, examples, and results, it is to be understood that the compounds, compositions, and methods of present disclosure are not limited in application to the details of specific embodiments and examples as set forth in the following description. The description provided herein is intended for purposes of illustration only and is not intended to be construed in a limiting sense. As such, the language used herein is intended to be given the broadest possible scope and meaning; and the embodiments and examples are meant to be exemplary, not exhaustive. Also, it is to be understood that the phraseology and terminology employed herein is for the purpose of description and should not be regarded as limiting unless otherwise indicated as so. Moreover, in the following detailed description, numerous specific details are set forth in order to provide a more thorough understanding of the present disclosure. However, it will be apparent to a person having ordinary skill in the art that the present disclosure may be practiced without these specific details. In other instances, features which are well known to persons of ordinary skill in the art have not been described in detail to avoid unnecessary complication of the description. It is intended that all alternatives, substitutions, modifications and equivalents apparent to those having ordinary skill in the art are included within the scope of the present disclosure. All of the compounds, compositions, and methods and application and uses thereof disclosed herein can be made and executed without undue experimentation in light of the present disclosure. Thus, while the compounds, compositions, and methods of the present disclosure have been described in terms of particular embodiments, it will be apparent to those of skill in the art that variations may be applied to the compounds, compositions, and methods and in the steps or in the sequence of steps of the methods described herein without departing from the concept, spirit, and scope of the inventive concepts.

All patents, published patent applications, and non-patent publications including published articles mentioned in the specification or referenced in any portion of this application, are herein expressly incorporated by reference in their entirety to the same extent as if each individual patent or publication was specifically and individually indicated to be incorporated by reference.

The following abbreviations may be used herein: ER, endoplasmic reticulum; UPR, unfolded protein response; INS-1 cell, rat insulinoma cell line; Tm, tunicamycin; SAR, structure-activity relationship; $EC_{50}$, half maximal effective concentration; THF, tetrahydrofuran; DIEA, N,N-diisopropylethylamine; RT-PCR, reverse transcription polymerase chain reaction; TUNEL, Terminal deoxynucleotidyl transferase dUTP nick end labeling; PARP, Poly(ADP-ribose) polymerase; PERK, PKR-like ER kinase; eIF2α, eukaryotic translation initiator factor 2α; ATF4, activating transcription factor 4; CHOP, C/EBP homologous protein; XBP1, X-box binding protein 1; ATF6, activating transcription factor 6; FBS, fetal bovine serum; PDX1, pancreatic and duodenal homeobox 1; MafA, v-maf musculoaponeurotic fibrosarcoma oncogene family, protein A; INS1, insulin 1; INS2, insulin 2; rt, room temperature.

The term "pharmaceutically acceptable" refers to compounds and compositions which are suitable for administration to humans and/or animals without undue adverse side effects such as toxicity, irritation and/or allergic response commensurate with a reasonable benefit/risk ratio. The compounds or conjugates of the present disclosure may be combined with one or more pharmaceutically-acceptable excipients, including carriers, vehicles, diluents, and adjuvents which may improve solubility, deliverability, dispersion, stability, and/or conformational integrity of the compounds or conjugates thereof.

The term "active agent" as used herein refers to 3-(N-piperidinyl) methyl benzamide compounds as described herein or an active conjugate thereof. A conjugate is a compound comprising an active agent covalently linked, directly or indirectly via a linker molecule, to a secondary compound. The active agent may be associated with a targeting moiety or molecule which is able to bind to a target cell or a portion of a target cell. The targeting moiety may be linked directly or indirectly to the active agent, or to the pharmaceutically acceptable carrier, vehicle, or diluent which contains or is associated with the active agent. The targeting moiety may be any molecule that can bind to another molecule. For example, a targeting moiety may include an antibody or its fragments, a receptor molecule, a chimeric antibody molecule, or an affinity reagent. As used herein, the term "targeting moiety" refers to a structure that binds or associates with a biological moiety or fragment thereof. As noted, in some embodiments, the targeting moiety may be an antibody. In some embodiments, the targeting moiety may be a monoclonal antibody (mAB). In some embodiments, the targeting moiety may be an antibody fragment, surrogate, or variant. In some embodiments, the targeting moiety may be a protein ligand. In some embodiments, the targeting moiety may be a protein scaffold. In some embodiments, the targeting moiety may be a peptide. In some embodiments, the targeting moiety may be RNA or DNA. In some embodiments, the targeting moiety may be a RNA or DNA fragment. In some embodiments, the targeting moiety may be a small molecule ligand.

As used herein, "pure," or "substantially pure" means an object species is the predominant species present (i.e., on a molar basis it is more abundant than any other object species in the composition thereof), and particularly a substantially purified fraction is a composition wherein the object species comprises at least about 50 percent (on a molar basis) of all macromolecular species present. Generally, a substantially pure composition will comprise more than about 80% of all macromolecular species present in the composition, more particularly more than about 85%, more than about 90%, more than about 95%, or more than about 99%. The term "pure" or "substantially pure" also refers to preparations where the object species is at least 60% (w/w) pure, or at least 70% (w/w) pure, or at least 75% (w/w) pure, or at least 80% (w/w) pure, or at least 85% (w/w) pure, or at least 90% (w/w) pure, or at least 92% (w/w) pure, or at least 95% (w/w) pure, or at least 96% (w/w) pure, or at least 97% (w/w) pure, or at least 98% (w/w) pure, or at least 99% (w/w) pure, or 100% (w/w) pure.

Non-limiting examples of animals within the scope and meaning of this term include dogs, cats, rats, mice, guinea pigs, chinchillas, horses, goats, cattle, sheep, zoo animals, Old and New World monkeys, non-human primates, and humans.

"Treatment" refers to therapeutic treatments. "Prevention" refers to prophylactic or preventative treatment measures or reducing the onset of a condition or disease. The term "treating" refers to administering the active agent to a subject for therapeutic purposes and/or for prevention. Non-limiting examples of modes of administration include oral, topical, retrobulbar, subconjunctival, transdermal, parenteral, subcutaneous, intranasal, intramuscular, intraperitoneal, intravitreal, and intravenous routes, including both local and systemic applications. In addition, the active agent of the present disclosure may be designed to provide delayed, controlled, extended, and/or sustained release using formulation techniques which are well known in the art.

The term "topical" is used herein to define a mode of administration through an epithelial surface, such as but not limited to, a material that is administered by being applied externally to the eye. A non-limiting example of topical administration is through the use of eyedrops.

The terms "therapeutic composition" and "pharmaceutical composition" refer to an active agent-containing composition that may be administered to a subject by any method known in the art or otherwise contemplated herein, wherein administration of the composition brings about a therapeutic effect as described elsewhere herein. In addition, the compositions of the present disclosure may be designed to provide delayed, controlled, extended, and/or sustained release using formulation techniques which are well known in the art.

The term "effective amount" refers to an amount of the active agent which is sufficient to exhibit a detectable therapeutic or treatment effect in a subject without excessive adverse side effects (such as substantial toxicity, irritation and allergic response) commensurate with a reasonable benefit/risk ratio when used in the manner of the present disclosure. The effective amount for a subject will depend upon the subject's type, size and health, the nature and severity of the condition to be treated, the method of administration, the duration of treatment, the nature of concurrent therapy (if any), the specific formulations employed, and the like. Thus, it is not possible to specify an exact effective amount in advance. However, the effective amount for a given situation can be determined by one of ordinary skill in the art using routine experimentation based on the information provided herein.

The term "ameliorate" means a detectable or measurable improvement in a subject's condition or or symptom thereof. A detectable or measurable improvement includes a subjective or objective decrease, reduction, inhibition, suppression, limit or control in the occurrence, frequency, severity, progression, or duration of the condition, or an improvement in a symptom or an underlying cause or a consequence of the condition, or a reversal of the condition. A successful treatment outcome can lead to a "therapeutic effect," or "benefit" of ameliorating, decreasing, reducing, inhibiting, suppressing, limiting, controlling or preventing the occurrence, frequency, severity, progression, or duration of a condition, or consequences of the condition in a subject.

A decrease or reduction in worsening, such as stabilizing the condition, is also a successful treatment outcome. A therapeutic benefit therefore need not be complete ablation or reversal of the condition, or any one, most or all adverse symptoms, complications, consequences or underlying causes associated with the condition. Thus, a satisfactory endpoint may be achieved when there is an incremental improvement such as a partial decrease, reduction, inhibition, suppression, limit, control or prevention in the occurrence, frequency, severity, progression, or duration, or inhibition or reversal of the condition (e.g., stabilizing), over a short or long duration of time (e.g., seconds, minutes, hours).

Unless otherwise defined herein, scientific and technical terms used in connection with the present disclosure shall have the meanings that are commonly understood by those having ordinary skill in the art. Further, unless otherwise required by context, singular terms shall include pluralities and plural terms shall include the singular. Where used herein, the specific term "single" is limited to only "one". Where used herein, the pronoun "we" is intended to refer to all persons involved in a particular aspect of the investigation disclosed herein and as such may include non-inventor laboratory assistants and collaborators working under the supervision of the inventor.

As utilized in accordance with the methods, compounds, and compositions of the present disclosure, the following terms, unless otherwise indicated, shall be understood to have the following meanings:

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or when the alternatives are mutually exclusive, although the disclosure supports a definition that refers to only alternatives and "and/or." The use of the term "at least one" will be understood to include one as well as any quantity more than one, including but not limited to, 2, 3, 4, 5, 6, 7, 8, 9, 10, 15, 20, 30, 40, 50, 100, or any integer inclusive therein. The term "at least one" may extend up to 100 or 1000 or more, depending on the term to which it is attached; in addition, the quantities of 100/1000 are not to be considered limiting, as higher limits may also produce satisfactory results. In addition, the use of the term "at least one of X, Y and Z" will be understood to include X alone, Y alone, and Z alone, as well as any combination of X, Y and Z.

As used herein, all numerical values or ranges include fractions of the values and integers within such ranges and fractions of the integers within such ranges unless the context clearly indicates otherwise. Thus, to illustrate, reference to a numerical range, such as 1-10 includes 1, 2, 3, 4, 5, 6, 7, 8, 9, 10, as well as 1.1, 1.2, 1.3, 1.4, 1.5, etc., and so forth. Reference to a range of 1-50 therefore includes 1, 2, 3, 4, 5, 6, 7, 8, 9, 10, 11, 12, 13, 14, 15, 16, 17, 18, 19, 20, etc., up to and including 50, as well as 1.1, 1.2, 1.3, 1.4, 1.5, etc., 2.1, 2.2, 2.3, 2.4, 2.5, etc., and so forth. Reference to a series of ranges includes ranges which combine the values of the boundaries of different ranges within the series. Thus, to illustrate reference to a series of ranges, for example, of 1-10, 10-20, 20-30, 30-40, 40-50, 50-60, 60-75, 75-100, 100-150, 150-200, 200-250, 250-300, 300-400, 400-500, 500-750, 750-1,000, includes ranges of 1-20, 10-50, 50-100, 100-500, and 500-1,000, for example. Reference to an integer with more (greater) or less than includes any number greater or less than the reference number, respectively. Thus, for example, reference to less than 100 includes 99, 98, 97, etc. all the way down to the number one (1); and less than 10 includes 9, 8, 7, etc. all the way down to the number one (1).

As used in this specification and claims, the words "comprising" (and any form of comprising, such as "comprise"

and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" as used herein refers to all permutations and combinations of the listed items preceding the term. For example, "A, B, C, or combinations thereof" is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, AAB, BBC, AAABCCCC, CBBAAA, CABABB, and so forth. The skilled artisan will understand that typically there is no limit on the number of items or terms in any combination, unless otherwise apparent from the context.

Throughout this application, the term "about" is used to indicate that a value includes the inherent variation of error for the composition, the method used to administer the active agent or composition, or the variation that exists among the study subjects. As used herein the qualifiers "about" or "approximately" are intended to include not only the exact value, amount, degree, orientation, or other qualified characteristic or value, but are intended to include some slight variations due to measuring error, manufacturing tolerances, stress exerted on various parts or components, observer error, wear and tear, and combinations thereof, for example. The term "about" or "approximately", where used herein when referring to a measurable value such as an amount, a temporal duration, and the like, is meant to encompass, for example, variations of ±20% or ±10%, or ±5%, or ±1%, or ±0.1% from the specified value, as such variations are appropriate to perform the disclosed methods and as understood by persons having ordinary skill in the art. As used herein, the term "substantially" means that the subsequently described event or circumstance completely occurs or that the subsequently described event or circumstance occurs to a great extent or degree. For example, the term "substantially" means that the subsequently described event or circumstance occurs at least 90% of the time, or at least 95% of the time, or at least 98% of the time.

As used herein any reference to "one embodiment" or "an embodiment" means that a particular element, feature, structure, or characteristic described in connection with the embodiment is included in at least one embodiment and may be included in other embodiments. The appearances of the phrase "in one embodiment" in various places in the specification are not necessarily all referring to the same embodiment and are not necessarily limited to a single or particular embodiment.

By "biologically active" is meant the ability of the active agent to modify the physiological system of an organism without reference to how the active agent has its physiological effects.

Effectiveness of a method or use, such as a treatment that provides a potential therapeutic benefit or improvement of a condition or disease, can be ascertained by various methods and testing assays.

The active agents disclosed herein can be used in the treatment of type 1 and type 2 diabetes, and other diseases or conditions involving ER stress, including neurodegenerative diseases such as Parkinson's disease, amyotrophic lateral sclerosis (ALS), Alzheimer's disease (AD), Huntington's disease, and progressive supra nuclear palsy (PSP). Other indications also include metabolic syndrome including obesity, atherosclerosis, chronic heart disease, stroke, ischemia-reperfusion injury, and cancer.

The active agents of the present disclosure may be present in the pharmaceutical compositions at any concentration that allows the pharmaceutical composition to function in accordance with the present disclosure; for example, but not by way of limitation, the active agents may be present in the composition in a range having a lower level selected from 0.0001%, 0.005%, 0.001%, 0.005%, 0.01%, 0.05%, 0.1%, 0.2%, 0.3%, 0.4%, 0.5%, 0.6%, 0.7%, 0.8%, 0.9%, 1.0%, 1.1%, 1.2%, 1.3%, 1.4%, 1.5%, 1.6%, 1.7%, 1.8%, 1.9% and 2.0%; and an upper level selected from 3%, 3.5%, 4%, 4.5%, 5%, 5.5%, 6%, 6.5%, 7%, 7.5%, 8%, 8.5%, 9%, 9.5%, 10%, 11%, 12%, 13%, 14%, 15%, 16%, 17%, 18%, 19%, 20%, 25%, 30%, 35%, 40%, 45%, 50%, 55%, 60%, 65%, 70%, 75%, 80%, 85%, 90%, and 95%. Non-limiting examples of particular ranges include a range of from about 0.0001% to about 95%, a range of from about 0.001% to about 75%; a range of from about 0.005% to about 50%; a range of from about 0.01% to about 40%; a range of from about 0.05% to about 35%; a range of from about 0.1% to about 30%; a range of from about 0.1% to about 25%; a range of from about 0.1% to about 20%; a range of from about 1% to about 15%; a range of from about 2% to about 12%; a range of from about 5% to about 10%; and the like. Any other range that includes a lower level selected from the above-listed lower level concentrations and an upper level selected from the above-listed upper level concentrations also falls within the scope of the present disclosure.

Suitable carriers, vehicles, and other components that may be included in the formulation are described, for example, in Remington: *The Science and Practice of Pharmacy*, $21^{st}$ Ed. and $22^{nd}$ Ed. The term "pharmaceutically acceptable" means that the carrier is a non-toxic material that does not interfere with the effectiveness of the biological activity of the active agent. The characteristics of the carrier will depend on various factors, including but not limited to, the route of administration.

For example, but not by way of limitation, the active agent may be dissolved in a physiologically acceptable pharmaceutical carrier or diluent and administered as either a solution or a suspension. Non-limiting examples of suitable pharmaceutically acceptable carriers include water, saline, dextrose solutions, fructose solutions, ethanol, or oils of animal, vegetative, or synthetic origin, or any combination thereof. A sterile diluent, which may contain materials generally recognized for approximating physiological conditions and/or as required by governmental regulations, may be employed as the pharmaceutically acceptable carrier. In this respect, the sterile diluent may contain a buffering agent to obtain a physiologically acceptable pH, such as (but not limited to) sodium chloride, saline, phosphate-buffered saline, and/or other substances which are physiologically acceptable and/or safe for use.

The pharmaceutical compositions may also contain one or more additional components in addition to the active agent and pharmaceutically acceptable carrier(s) (and other additional therapeutically active agent(s), if present). Examples of additional components that may be present include, but are not limited to, diluents, fillers, salts, buffers, preservatives, stabilizers, solubilizers, and other materials well known in the art. Another particular non-limiting example of an additional component that may be present in the pharmaceutical composition is a delivery agent, as discussed in further detail herein below.

Other embodiments of the pharmaceutical compositions of the present disclosure may include the incorporation or entrapment of the active agent in various types of drug delivery systems that function to provide targeted delivery, controlled release, and/or increased half-life to the active agent. For example, but not by way of limitation, it is possible to entrap the active agent in microcapsules prepared by coacervation techniques or by interfacial polymerization (for example, hydroxymethylcellulose or gelatin-microcapsules and poly-(methylmethacylate) microcapsules, respectively). It is also possible to entrap the active agent in macroemulsions or colloidal drug delivery systems (such as but not limited to, liposomes, albumin microspheres, microemulsions, nanoparticles, nanocapsules, and the like). Such techniques are well known to persons having ordinary skill in the art, and thus no further description thereof is deemed necessary.

In one particular, non-limiting example, the pharmaceutical composition may include a liposome in which the active agent is disposed. In addition to other pharmaceutically acceptable carrier(s), the liposome may contain amphipathic agents such as lipids which exist in an aggregated form as micelles, insoluble monolayers, liquid crystals, or lamellar layers in aqueous solution. Suitable lipids for liposomal formulation include, but are not limited to, monoglycerides, diglycerides, sulfatides, lysolecithin, phospholipids, saponin, bile acids, combinations thereof, and the like. Preparation of such liposomal formulations is well within the level of ordinary skill in the art, as disclosed, for example, in U.S. Pat. Nos. 4,235,871; 4,501,728; 4,837,028; and 4,737,323; the entire contents of each of which are incorporated herein by reference.

In other non-limiting examples, the active agent of the present disclosure may be incorporated into particles of one or more polymeric materials, as this type of incorporation can be useful in controlling the duration of action of the active agent by allowing for controlled release from the preparations, thus increasing the half-life thereof. Non-limiting examples of polymeric materials that may be utilized in this manner include polyesters, polyamides, polyamino acids, hydrogels, poly(lactic acid), ethylene vinylacetate copolymers, copolymer micelles of, for example, PEG and poly(l-aspartamide), and combinations thereof.

The pharmaceutical compositions described or otherwise contemplated herein may further comprise at least one delivery agent, such as a targeting moiety, that assists in delivery of the active agent to a desired site of delivery, such as a pancreatic beta cell.

The compositions of the present disclosure may be formulated for administration by any other method known or otherwise contemplated in the art, as long as the route of administration allows for delivery of the active agent so that the compounds can function in accordance with the present disclosure, e.g., to reduce ER stress. Examples of other routes of administration include, but are not limited to, oral, topical, retrobulbar, subconjunctival, transdermal, parenteral, subcutaneous, intranasal, intramuscular, intraperitoneal, intravitreal, and intravenous routes, including both local and systemic application routes.

Another non-limiting embodiment of the present disclosure is directed to a kit that contain one or more of any of the pharmaceutical compositions described or otherwise contemplated herein. The kit may further contain a second agent as described herein above for use concurrently with the pharmaceutical composition(s). If the composition present in the kit is not provided in the form in which it is to be delivered, the kit may further contain a pharmaceutically acceptable carrier, vehicle, diluent, or other agent for mixing with the active agent for preparation of the pharmaceutical composition. The kit including the composition and/or other reagents may also be packaged with instructions packaged for administration and/or dosing of the compositions contained in the kit. The instructions may be fixed in any tangible medium, such as printed paper, or a computer-readable magnetic or optical medium, or instructions to reference a remote computer data source such as a world-wide web page accessible via the internet.

The kit may contain single or multiple doses of the pharmaceutical composition which contains the active agent. When multiple doses are present, the doses may be disposed in bulk within a single container, or the multiple doses may be disposed individually within the kit; that is, the pharmaceutical compositions may be present in the kit in unit dosage forms to facilitate accurate dosing. The term "unit dosage forms" as used herein refers to physically discrete units suitable as unitary dosages for human subjects and other mammals; each unit contains a predetermined quantity of the active agent calculated to produce the desired therapeutic effect, in association with a suitable pharmaceutical excipient. Typical unit dosage forms of liquid compositions include prefilled, premeasured ampules or syringes; for solid compositions, typical unit dosage forms include pills, tablets, capsules, or the like. In such compositions, the active agent may sometimes be a minor component (from about 0.1 to about 50% by weight, such as but not limited to, from about 1 to about 40% by weight) with the remainder being various vehicles or carriers and processing aids helpful for forming the desired dosing form.

The active agent may be provided as a "pharmaceutically acceptable salt," which refers to salts that retain the biological effectiveness and properties of a compound and, which are not biologically or otherwise undesirable for use in a pharmaceutical. In many cases, the compounds disclosed herein are capable of forming acid and/or base salts by virtue of the presence of amino and/or carboxyl groups or groups similar thereto. Pharmaceutically acceptable acid addition salts can be formed with inorganic acids and organic acids. Inorganic acids from which salts can be derived include, for example, hydrochloric acid, hydrobromic acid, sulfuric acid, nitric acid, phosphoric acid, and the like. Organic acids from which salts can be derived include, for example, acetic acid, propionic acid, glycolic acid, pyruvic acid, oxalic acid, maleic acid, malonic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, and the like. Pharmaceutically acceptable base addition salts can be formed with inorganic and organic bases. Inorganic bases from which salts can be derived include, for example, sodium, potassium, lithium, ammonium, calcium, magnesium, iron, zinc, copper, manganese, aluminum, and the like; particularly preferred are the ammonium, potassium, sodium, calcium and magnesium salts. Organic bases from which salts can be derived include, for example, primary, secondary, and tertiary amines, substituted amines including naturally occurring substituted amines, cyclic amines, basic ion exchange resins, and the like, specifically such as isopropylamine, trimethylamine, diethylamine, triethylamine, tripropylamine, and ethanolamine. Many such salts are known in the art, as described in WO 87/05297, Johnston et al., published Sep. 11, 1987 (incorporated by reference herein in its entirety).

The amount of the active agent that is effective in the treatment described herein can be determined by the attending diagnostician, as one of ordinary skill in the art, by the use of conventional techniques and by observing results obtained under analogous circumstances. In determining the therapeutically effective dose, a number of factors may be considered by the attending diagnostician, including, but not limited to: the species of the subject; its size, age, and general health; the specific diseases or other conditions involved; the degree, involvement, and/or severity of the diseases or conditions; the response of the individual subject; the particular active agent administered; the mode of administration; the bioavailability characteristics of the preparation administered; the dose regimen selected; the use of concomitant medication; and other relevant circumstances. A therapeutically effective amount of an active agent of the present disclosure also refers to an amount of the active agent which is effective in controlling, reducing, or ameliorating the condition to be treated.

Practice of the method of the present disclosure may include administering to a subject a therapeutically effective amount of the pharmaceutical composition (containing the active agent in any suitable systemic and/or local formulation, in an amount effective to deliver the dosages listed above. The dosage can be administered, for example, but not by way of limitation, on a one-time basis, or administered at multiple times (for example, but not by way of limitation, from one to five times per day, or once or twice per week). The pharmaceutical composition may be administered either alone or in combination with other therapies, in accordance with the inventive concepts disclosed herein.

Compositions of the active agent can be administered in a single dose treatment or in multiple dose treatments on a schedule and over a time period appropriate to the age, weight and condition of the subject, the particular composition used, and the route of administration. In one embodiment, a single dose of the composition according to the disclosure is administered. In other embodiments, multiple doses are administered. The frequency of administration can vary depending on any of a variety of factors, e.g., severity of the symptoms, degree of immunoprotection desired, or whether the composition is used for prophylactic or curative purposes. For example, in certain embodiments, the composition is administered once per month, twice per month, three times per month, every other week, once per week, twice per week, three times per week, four times per week, five times per week, six times per week, every other day, daily, twice a day, or three times a day. The duration of treatment, e.g., the period of time over which the composition is administered, can vary, depending on any of a variety of factors, e.g., subject response. For example, the composition can be administered over a period of time ranging from about one day to about one week, from about two weeks to about four weeks, from about one month to about two months, from about two months to about four months, from about four months to about six months, from about six months to about eight months, from about eight months to about 1 year, from about 1 year to about 2 years, or from about 2 years to about 4 years, or more.

The compositions can be combined with a pharmaceutically acceptable carrier (excipient) or vehicle to form a pharmacological composition. Pharmaceutically acceptable carriers can contain a physiologically acceptable compound that acts to, e.g., stabilize, or increase or decrease the absorption or clearance rates of the pharmaceutical compositions. Physiologically acceptable carriers and vehicles can include, for example, carbohydrates, such as glucose, sucrose, or dextrans, antioxidants, such as ascorbic acid or glutathione, chelating agents, low molecular weight proteins, detergents, liposomal carriers, or excipients or other stabilizers and/or buffers. Other physiologically acceptable compounds, carriers, and vehicles include wetting agents, emulsifying agents, dispersing agents or preservatives.

When administered orally, the present compositions may be protected from digestion. This can be accomplished either by complexing the active agent with a composition to render it resistant to acidic and enzymatic hydrolysis or by packaging active agent in an appropriately resistant carrier such as a liposome, e.g., such as shown in U.S. Pat. No. 5,391,377.

For transmucosal or transdermal administration, penetrants appropriate to the barrier to be permeated can be used in the formulation. Such penetrants are generally known in the art, and include, e.g., for transmucosal administration, bile salts and fusidic acid derivatives. In addition, detergents can be used to facilitate permeation. Transmucosal administration can be through nasal sprays or using suppositories. For topical, transdermal administration, the agents are formulated into ointments, creams, salves, powders and gels. Transdermal delivery systems can also include, e.g., patches. The present compositions can also be administered in sustained delivery or sustained release mechanisms. For example, biodegradeable microspheres or capsules or other biodegradeable polymer configurations capable of sustained delivery of the active agent can be included herein.

For inhalation, the active agent can be delivered using any system known in the art, including dry powder aerosols, liquids delivery systems, air jet nebulizers, propellant systems, and the like. For example, the pharmaceutical formulation can be administered in the form of an aerosol or mist. For aerosol administration, the formulation can be supplied in finely divided form along with a surfactant and propellant. In another aspect, the device for delivering the formulation to respiratory tissue is an inhaler in which the formulation vaporizes. Other liquid delivery systems include, e.g., air jet nebulizers.

The active agent can be delivered alone or as pharmaceutical compositions by any means known in the art, e.g., systemically, regionally, or locally; by intra-arterial, intrathecal (IT), intravenous (IV), parenteral, intra-pleural cavity, topical, oral, or local administration, as subcutaneous, intratracheal (e.g., by aerosol) or transmucosal (e.g., buccal, bladder, vaginal, uterine, rectal, nasal mucosa).

In one aspect, the pharmaceutical formulations comprising the active agent are incorporated in lipid monolayers or bilayers, e.g., liposomes, such as shown in U.S. Pat. Nos. 6,110,490; 6,096,716; 5,283,185; and 5,279,833. Liposomes and liposomal formulations can be prepared according to standard methods and are also well known in the art, such as U.S. Pat. Nos. 4,235,871; 4,501,728 and 4,837,028.

In one aspect, the active agent is prepared with one or more carriers that will protect the active agent against rapid elimination from the body, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, and polylactic acid. Methods for preparation of such formulations will be apparent to those skilled in the art.

The active agent in general may be formulated to obtain compositions that include one or more pharmaceutically suitable excipients, surfactants, polyols, buffers, salts, amino acids, or additional ingredients, or some combination of these. This can be accomplished by known methods to prepare pharmaceutically useful dosages, whereby the active agent is combined in a mixture with one or more pharmaceutically suitable excipients. Sterile phosphate-buffered saline is one example of a pharmaceutically suitable excipient.

Examples of routes of administration of the active agents described herein include parenteral injection, e.g., by subcutaneous, intramuscular or transdermal delivery. Other forms of parenteral administration include intravenous, intraarterial, intralymphatic, intrathecal, intraocular, intracerebral, or intracavitary injection. In parenteral administration, the compositions will be formulated in a unit dosage injectable form such as a solution, suspension or emulsion, in association with a pharmaceutically acceptable excipient. Such excipients are inherently nontoxic and nontherapeutic. Examples of such excipients are saline, Ringer's solution, dextrose solution and Hanks' solution. Nonaqueous excipients such as fixed oils and ethyl oleate may also be used. An alternative excipient is 5% dextrose in saline. The excipient may contain minor amounts of additives such as substances that enhance isotonicity and chemical stability, including buffers and preservatives.

Formulated compositions comprising the active agent can be used for subcutaneous, intramuscular or transdermal administration. Compositions can be presented in unit dosage form, e.g., in ampoules or in multi-dose containers, with an added preservative. Compositions can also take such forms as suspensions, solutions or emulsions in oily or aqueous vehicles, and can contain formulatory agents such as suspending, stabilizing and/or dispersing agents. Alternatively, the compositions can be in powder form for constitution with a suitable vehicle, e.g., sterile pyrogen-free water, before use.

The active agents may be administered in solution. The formulation thereof may be in a solution having a suitable pharmaceutically acceptable buffer such as phosphate, Tris (hydroxymethyl) aminomethane-HCl or citrate, and the like. Buffer concentrations should be in the range of 1 to 100 mM. The formulated solution may also contain a salt, such as sodium chloride or potassium chloride in a concentration of 50 to 150 mM. An effective amount of a stabilizing agent such as mannitol, trehalose, sorbitol, glycerol, albumin, a globulin, a detergent, a gelatin, a protamine or a salt of protamine may also be included.

For example, but not by way of limitation, the therapeutically effective amount of an active agent used in the present disclosure will generally contain sufficient active agent to deliver in a range of from about 0.01 µg/kg to about 10 mg/kg (weight of active agent/body weight of patient). For example, but not by way of limitation, the composition will deliver about 0.1 µg/kg to about 5 mg/kg, and more particularly about 1 µg/kg to about 1 mg/kg.

Exemplary, non-limiting ranges for a therapeutically or prophylactically effective amount of the active agent include but are not limited to 0.001 mg/kg of the subject's body weight to 100 mg/kg of the subject's body weight, more typically 0.01 mg/kg to 100 mg/kg, 0.1 mg/kg to 50 mg/kg, 0.1 mg/kg to 40 mg/kg, 1 mg/kg to 30 mg/kg, or 1 mg/kg to 20 mg/kg, or 2 mg/kg to 30 mg/kg, 2 mg/kg to 20 mg/kg, 2 mg/kg to 15 mg/kg, 2 mg/kg to 12 mg/kg, or 2 mg/kg to 10 mg/kg, or 3 mg/kg to 30 mg/kg, 3 mg/kg to 20 mg/kg, 3 mg/kg to 15 mg/kg, 3 mg/kg to 12 mg/kg, or 3 mg/kg to 10 mg/kg, or 5 mg to 1500 mg, as a fixed dosage.

The composition is formulated to contain an effective amount of the active agent, wherein the amount depends on the animal to be treated and the condition to be treated. In certain embodiments, the active agent is administered at a dose ranging from about 0.001 mg to about 10 g, from about 0.01 mg to about 10 g, from about 0.1 mg to about 10 g, from about 1 mg to about 10 g, from about 1 mg to about 9 g, from about 1 mg to about 8 g, from about 1 mg to about 7 g, from about 1 mg to about 6 g, from about 1 mg to about 5 g, from about 10 mg to about 10 g, from about 50 mg to about 5 g, from about 50 mg to about 5 g, from about 50 mg to about 2 g, from about 0.05 µg to about 1.5 mg, from about 10 µg to about 1 mg protein, from about 30 µg to about 500 µg, from about 40 µg to about 300 µg, from about 0.1 µg to about 200 mg, from about 0.1 µg to about 5 µg, from about 5 µg to about 10 µg, from about 10 µg to about 25 µg, from about 25 µg to about 50 µg, from about 50 µg to about 100 µg, from about 100 µg to about 500 µg, from about 500 µg to about 1 mg, from about 1 mg to about 2 mg. The specific dose level for any particular subject depends upon a variety of factors including the activity of the specific peptide, the age, body weight, general health, sex, diet, time of administration, route of administration, and rate of excretion, drug combination and the severity of the particular disease undergoing therapy.

The dosage of an administered active agent for humans will vary depending upon such factors as the patient's age, weight, height, sex, general medical condition and previous medical history. In certain non-limiting embodiments, the recipient is provided with a dosage of the active agent that is in the range of from about 1 mg to 1000 mg as a single infusion or single or multiple injections, although a lower or higher dosage also may be administered. The dosage may be in the range of from about 25 mg to 100 mg of the active agent per square meter ($m^2$) of body surface area for a typical adult, although a lower or higher dosage also may be administered. Examples of dosages that may be administered to a human subject further include, for example, 1 to 500 mg, 1 to 70 mg, or 1 to 20 mg, although higher or lower doses may be used. Dosages may be repeated as needed, for example, once per week for 4-10 weeks, or once per week for 8 weeks, or once per week for 4 weeks. It may also be given less frequently, such as every other week for several months, or more frequently, such as twice weekly or by continuous infusion.

Where used herein alkyls, alkoxyls, haloalkyls, and haloalkoxyls are generally intended to refer to molecules having hydrocarbon chains that comprise 1, 2, 3, 4, 5, 6, 7, 8, 9, 10, 11, or 12 carbons, unless otherwise designated. The hydrocarbon chains may be straight or branched. Examples of alkyls include but are not limited to methyl, ethyl, propyl, isopropyl, and butyl. Alkoxy denotes an alkyl group which is linked to an oxygen atom. Examples of alkoxyls include but are not limited to methoxyl, ethoxyl, propoxyl, isopropoxyl, and butoxyl. Haloalkyls and haloalkoxyls are alkyls and alkoxyls which comprise at least one halogen atom such as chlorine, fluorine, bromine, or iodine.

EXAMPLES

Certain novel embodiments of the present disclosure, having now been generally described, will be more readily understood by reference to the following examples, which are included merely for purposes of illustration of certain aspects and embodiments of the present disclosure, and are not intended to be limiting. The following detailed examples are to be construed, as noted above, only as illustrative, and not as limiting of the present disclosure in any way whatsoever. Those skilled in the art will promptly recognize appropriate variations from the various compositions, structures, components, procedures and methods.

In at least certain embodiments, the present disclosure includes compounds and methods of treating disorders and conditions related to ER stress, including, but not limited to type 1 diabetes and type 2 diabetes (or others disorders or conditions described elsewhere herein). The compound may be an (N-piperidinyl) methyl benzamide derivative compound having the chemical structure I:

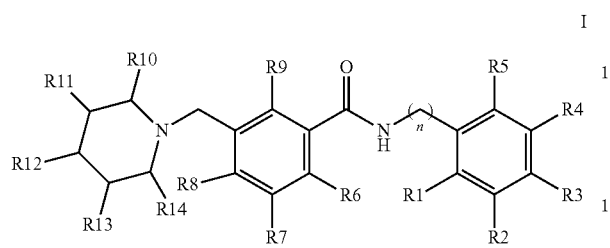

I wherein, in at least certain embodiments, the $R_1$-$R_{14}$ substituents of chemical structure I are independently selected from, but not limited to, the group consisting of hydrogen (H), hydroxyl (OH), halogens (halos) including chlorine (Cl), fluorine (F), bromine (Br), iodine (I), alkyls, alkoxys, haloalkyls (including mono, di, and trihaloalkyls), and haloalkoxyl (including mono, di, and trihaloalkoxyls), and n=1-10 carbons, i.e, 1, 2, 3, 4, 5, 6, 7, 8, 9, or 10 $CH_2$ moieties.

Experimental

In the present work, a β-cell survival-based high throughput screening approach was initially used to identify small molecules that protect β-cells against ER stress-induced apoptosis. Using a rat INS-1 β-cell assay for β-cell-protective activity against ER stress, the small molecule compound N-(3-chlorophenethyl)-2,3-dihydrobenzo[b][1,4]dioxine-6-carboxamide (1), a benzamide derivative, was discovered, from ~50,000 compounds screened, to be β-cell-protective against ER stress.

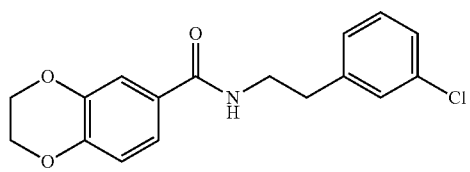

1

Although 1 is structurally novel, it has relatively weak activity on β-cell-protection (the maximum activity is 42% with an $EC_{50}$ value at 21 μM) prompted further study into the β-cell-protection properties of this novel class of compounds. A structure-activity-relationship (SAR) study was thus conducted to improve the weak potency of lead compound 1. Newly synthesized or commercially available compounds were tested for their β-cell-protective activity against ER stress in rat INS-1 β-cells. Treatment of INS-1 β-cells with tunicamycin (Tm), a potent ER stress inducer that inhibits N-linked glycosylation of proteins and causes the accumulation of misfolded proteins, significantly reduced cell viability at 72 h compared with DMSO-treated cells, as measured by an intracellular ATP level-based cell viability assay. The maximum activities and the concentrations that reach half-maximal activity ($EC_{50}$) of the compounds were evaluated by the degree of increase in viability of INS-1 cells co-treated with the compounds in the presence of Tm compared with Tm treatment alone. Maximum activity value in the tables is reported as % rescue from Tm (0.1 μg/mL)-induced reduction of cell viability. The values for Tm treatment alone and control (DMSO, without Tm) treatment are designated as 0% and 100%, respectively in all tables. $EC_{50}$ values (the concentrations that reach half-maximal activity) for INS-1 cell viability were calculated with GraphPad Prism from the data of ten 2-fold serial titration points in all tables. All experiments were performed in triplicate in all tables.

The initial focus was to modify the $R_2$ of the right phenyl ring of 1 while keeping the left dihydrobenzodioxine ring intact (Chemical structure II, Table 1).

TABLE 1

Derivatives of chemical structure II: Activity of compounds 8a-8h on the survival of INS-1 cells treated with Tm.

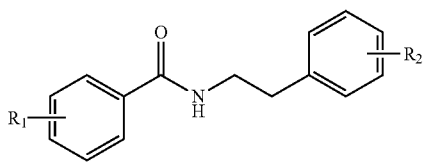

II

| Compd | $R_1$ | $R_2$ | Maximum activity (% rescue) | $EC_{50}$ (μM) |
|---|---|---|---|---|
| 1 | 3,4- | 3-Cl | 42% ± 12% | 21 ± 5.7 |
| 8a | 3,4- | H | 47% ± 9% | 19 ± 6.9 |
| 8b | 3,4- | 2-OMe | 29% ± 6% | >30 |
| 8c | 3,4- | 4-F | 50% ± 11% | 21 ± 3.2 |
| 8d | 3,4- | 4-Cl | 51% ± 17% | 15 ± 1.6 |
| 8e | 3,4- | 4-OMe | 26% ± 8% | >30 |
| 8f | 3,4- | 3,4-Di-OMe | 5% ± 7% | >30 |

TABLE 1-continued

Derivatives of chemical structure II: Activity of compounds 8a-8h on the survival of INS-1 cells treated with Tm.

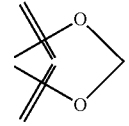

II

| Compd | R₁ | R₂ | Maximum activity (% rescue) | EC$_{50}$ (μM) |
|---|---|---|---|---|
| 8g | (dioxolane structure) | 3-Cl | 41% ± 14% | 25 ± 5.2 |
| 8h | 3,4-Di-OMe | 3-Cl | 46% ± 17% | 24 ± 2.1 |

While removal of the 3-chloro group in the right phenyl ring of 1 (8a) did not markedly affect the EC$_{50}$ values and maximum activity levels of the resultant compound, the introduction of a methoxy group, such as 2-methoxy (8b), 4-methoxy (8e), and 3,4-dimethoxy (8f), led to less potency in that an increase in the EC$_{50}$ values and reduction in the maximum activity were observed compared to the parent compound 1. However, replacement with 4-fluorine (8c) and 4-chlorine (8d) on the position 4 in the right phenyl ring appeared to improve the maximum activity levels of these compounds (42% for 1 to 50% for 8c and 51% for 8d) with a similar EC$_{50}$ values.

We then investigated the consequence of modifying the middle linker region, with the ethylene linker shortened to a methylene linker (Chemical structure III, Table 2). We found that the methylene derivatives with modifications at position 2 (2-chlorine (9a) and 2-bromo (9b)) exhibited similar activity to that of hit compound 1. However, the methylene derivatives with modifications at positions 3 and 4, such as 3-chlorine (9c), 3-bromo (9d), 4-chlorine (9e), and 3,4-dichlorine (9f), exhibited significantly improved EC$_{50}$ values and maximum activity compared to the ethylene linker derivatives (Table 2 vs. Table 1). Of note, compound 9e improved its EC$_{50}$ value over its ethylene counterpart 8d by almost 6-fold (EC$_{50}$ 2.8 μM for 9e vs. 15 μM for 8d) and the maximum activity (69% for 9e vs. 51% for 8d). Thus, the methylene group appeared to be a preferable linker.

TABLE 2

Derivatives of chemical structure III: Activity of compounds 9a-9f on the survival of INS-1 cells treated with Tm.

III

| Compd | R | Maximum activity (% rescue) | EC$_{50}$ (μM) |
|---|---|---|---|
| 9a | 2-Cl | 43% ± 12% | 25 ± 6.9 |
| 9b | 2-Br | 38% ± 14% | 25 ± 2.1 |

TABLE 2-continued

Derivatives of chemical structure III: Activity of compounds 9a-9f on the survival of INS-1 cells treated with Tm.

III

| Compd | R | Maximum activity (% rescue) | EC$_{50}$ (μM) |
|---|---|---|---|
| 9c | 3-Cl | 57% ± 11% | 9.5 ± 1.2 |
| 9d | 3-Br | 69% ± 9% | 5.5 ± 0.7 |
| 9e | 4-Cl | 69% ± 12% | 2.8 ± 0.5 |
| 9f | 3,4-Di-Cl | 68% ± 10% | 3.6 ± 0.9 |

Next, we shifted our SAR study to the left phenyl ring of N-phenethylbenzamide derivatives (Chemical structure IV, Table 3). Since removal of the 3-chloro group on the right ring did not appear to affect the potency (8a vs. 1), we kept the right phenyl ring unsubstituted. The resulting compounds with various substituents at the left phenyl ring are listed in Table 3. Most derivatives exhibited similar or reduced maximum activity or EC$_{50}$ values compared with the dihydrobenzodioxine derivative 8a. However, the 4-(N-piperidinyl)methyl group derivative (10l) exhibited significantly improved maximum activity (87% for 10l vs. 47% for 8a) and a similar EC$_{50}$ value (21 μM for 10l vs. 19 μM for 8a). In contrast, introduction of a 4-(N-pyrrolidinyl)methyl group (10k) resulted in a reduced maximum activity (31%). Taken together, these results indicate that the 4-(N-piperidinyl)methyl group rendered favorable activity to the scaffold.

TABLE 3

Derivatives of chemical structure IV: Activity of compounds 10a-10p on the survival of INS-1 cells treated with Tm.

IV

| Compd | R | Maximum activity (% rescue) | EC$_{50}$(μM) |
|---|---|---|---|
| 10a | 2-Me | 6% ± 5% | — |
| 10b | 2-S—iPr | 30% ± 8% | >30 |
| 10c | 3-F | <0 | — |
| 10d | 3-NO₂ | <0 | — |
| 10e | 3-NH₂ | <0 | — |
| 10f | 3-OEt | 49% ± 11% | 26 ± 4.5 |
| 10g | 3-NHSO₂Me | 24% ± 8% | 25 ± 2.1 |
| 10h | 4-Me | 25% ± 5% | 20 ± 5.4 |
| 10i | 4-O-propargyl | 54% ± 8% | >30 |
| 10j | 4SO₂-NMe₂ | 37% ± 6% | 19 ± 2.1 |
| 10k | 4-(N-pyrrolidinyl)methyl | 31% ± 7% | 11 ± 1.9 |
| 10l | 4-(N-piperidinyl)methyl | 87% ± 9% | 21 ± 3.5 |
| 10m | 3,4-Di-Cl | 42% ± 11% | 17 ± 6.1 |
| 10n | 3-Me-4-OMe | 56% ± 8% | 15 ± 3.2 |
| 10o | 2,3,4-trifluoro | 23% ± 6% | 9.9 ± 2.1 |
| 10p | 2,3,4,5-tetrafluoro | <0 | — |

Since we observed more favorable activity of the methylene middle linker than ethylene derivatives in compounds with dihydrobenzodioxine ring for the left phenyl moiety, derivatives were made to investigate whether a methylene middle linker would exhibit similar advantage in the 4-(N-piperidinyl)methyl background (Chemical structure V, Table 4). As summarized in Table 4, all the derivatives (11a-11d) exhibited significant maximum activity levels (all greater than 70%) regardless of the middle linker region. However, the derivatives with methylene middle linker exhibited significant improvements on the $EC_{50}$ values over the ethylene derivatives (11c vs. 11a and 11d vs. 11b). In particular, the $EC_{50}$ value of methylene derivative with 3,4-di-chlorine substitution in the right phenyl ring (11d) improved by 13-fold compared to that of the corresponding ethylene derivative 11b ($EC_{50}$ 1.8±0.2 µM for 11d vs. 24±2.7 µM for 11b). These results indicate that the combination of the 4-(N-piperidinyl)methyl moiety in the left phenyl ring and the methylene middle linker confers the compound favorable activity on β-cell protection.

TABLE 4

Derivatives of chemical structure V: Activity of compounds 10l, 11a-11d on the survival of INS-1 cells treated with Tm.

V

| Compd | n | R | Maximum activity (% rescue) | $EC_{50}$ (µM) |
|---|---|---|---|---|
| 10l | 2 | H | 87% ± 6% | 21 ± 3.5 |
| 11a | 2 | 4-Cl | 82% ± 10% | 21 ± 4.2 |
| 11b | 2 | 3,4-Di-Cl | 71% ± 11% | 24 ± 2.7 |
| 11c | 1 | 4-Cl | 77% ± 7% | 9.5 ± 1.1 |
| 11d | 1 | 3,4-Di-Cl | 78% ± 10% | 1.8 ± 0.2 |

We next investigated whether the position of the (N-piperidinyl)methyl group in the left phenyl ring affects β-cell-protective activity while keeping the methylene middle linker. A series of (N-piperidinyl)methyl benzamide derivatives (12a-12h, 13a-13d) were subsequently synthesized and tested (Chemical structure VI, Table 5). Clearly, substitution of (N-piperidinyl)methyl group at position 3 (12b-12e) showed significant improvements over positions 2 and 4 (12a, and 12f-12h) in both maximum activity and $EC_{50}$ values. Furthermore, we noticed that among the 3-(N-piperidinyl)methyl derivatives (12c-12e), substitutions with chlorine at meta and para positions in the right-hand phenyl ring (12d and 12e) improved the $EC_{50}$s over the ortho-substituted derivative 12c. We finally examined whether the electron status in the right phenyl ring influences the potency on the 3-(N-piperidinyl)methyl derivatives. We therefore substituted the compounds with the electron-donating group —OMe (13a and 13b) and the electron-withdrawing group —$CF_3$ (13c and 13d) at the meta- and para-positions on the right-hand phenyl ring. The electron-withdrawing groups, —$CF_3$ (13c and 13d) and —Cl (12d and 12e) at the meta- and para-positions significantly exhibited more favorable $EC_{50}$s compared to their electron-donating group (—OMe) counterparts (13a and 13b). In particular, the compound with the substitution of the strong electron-withdrawing $CF_3$ in the para-position (13d) exhibited the most potent property with a near 100% maximum activity and an $EC_{50}$ at 0.032 µM. We therefore chose 13d for further characterization of its mechanism of action in promoting β-cell survival and function against ER stress.

TABLE 5

Derivatives of chemical structure VI: Activity of compounds 12a-12h, 13a-d on the survival of INS-1 cells treated with Tm.

VI

| Compd | Substitution position of (N-piperidinyl) methyl | R | Maximum activity (% rescue) | $EC_{50}$ (µM) |
|---|---|---|---|---|
| 12a | 2 | 4-Cl | 73% ± 13% | 6.9 ± 1.2 |
| 12b | 3 | H | 95% ± 8% | 0.352 ± 0.062 |
| 12c | 3 | 2-Cl | 93% ± 7% | 2.04 ± 0.18 |
| 12d | 3 | 3-Cl | 90% ± 11% | 0.405 ± 0.057 |
| 12e | 3 | 4-Cl | 93% ± 13% | 0.24 ± 0.06 |
| 12f | 4 | 2-Cl | 87% ± 15% | 13 ± 1.6 |
| 12g | 4 | 3-Cl | 80% ± 9% | 2.2 ± 0.3 |
| 12h | 4 | 3-Br | 81% ± 12% | 4.9 ± 0.7 |
| 13a | 3 | 3-OMe | 92% ± 10% | 0.964 ± 0.135 |
| 13b | 3 | 4-OMe | 93% ± 5% | 1.12 ± 0.21 |
| 13c | 3 | 3-$CF_3$ | 91% ± 14% | 0.246 ± 0.043 |
| 13d | 3 | 4-$CF_3$ | 97% ± 8% | 0.032 ± 0.009 |

Figure 1:
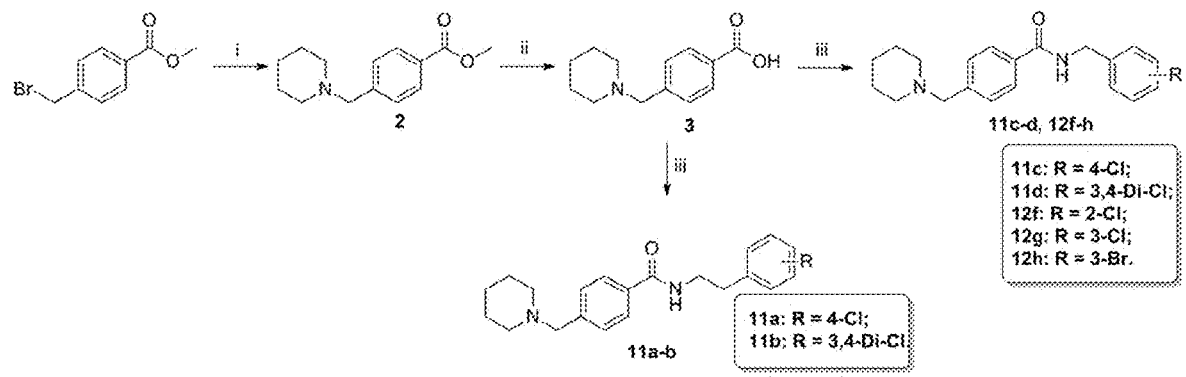
FIG. 1 shows schemes (1-3) for the synthesis of 4-, 3-, and 2-(N-piperidinyl)methyl benzamide derivatives. Scheme 1: Synthesis of 4-(N-piperidinyl)methyl benzamide compounds 11a-d and 12f-h. Reagents and conditions used were: (reaction i) piperidine, $CH_2Cl_2$, reflux, 75%; (reaction ii) NaOH, $MeOH/H_2O$, rt, 87%; and (reaction iii) benzylamines or phenylethylamines, HATU, DIEA, $CH_2Cl_2$, rt, 70-80%. Scheme 2: Synthesis of 3-(N-piperidinyl)methyl benzamide compounds 12b-e and 13a-d. Reagents and conditions: (reaction i) piperidine, $CH_2Cl_2$, reflux, 71%; (reaction ii) NaOH, $MeOH/H_2O$, rt, 83%; (reaction iii) benzylamines or phenylethylamines, HATU, DIEA, $CH_2Cl_2$, rt, 75-85%. Scheme 3: Synthesis of 2-(N-piperidinyl)methyl benzamide derivative 12a. Reagents and conditions: (reaction i) piperidine, $K_2CO_3$, THF, rt, 76%; (reaction ii) NaOH, $MeOH/H_2O$, rt, 89%; (reaction iii) 4-chlorobenzylamine, HATU, DIEA, $CH_2Cl_2$, rt, 73%.
Figure 1:
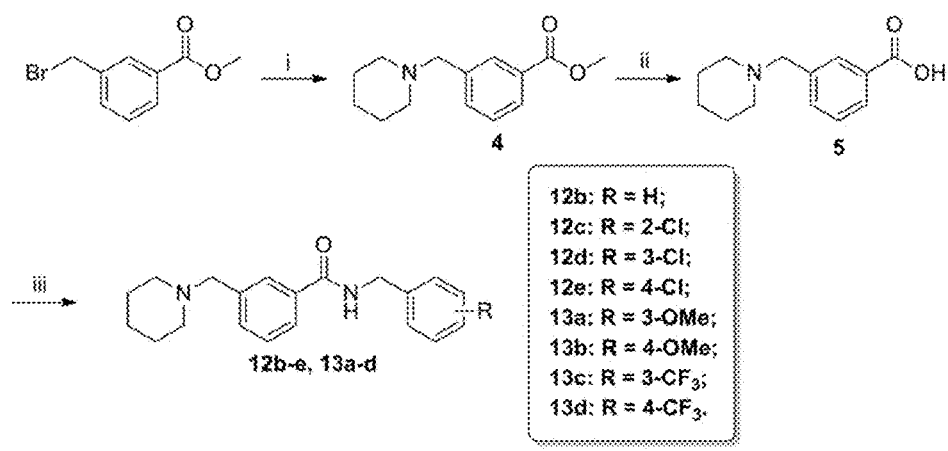
Figure 1:
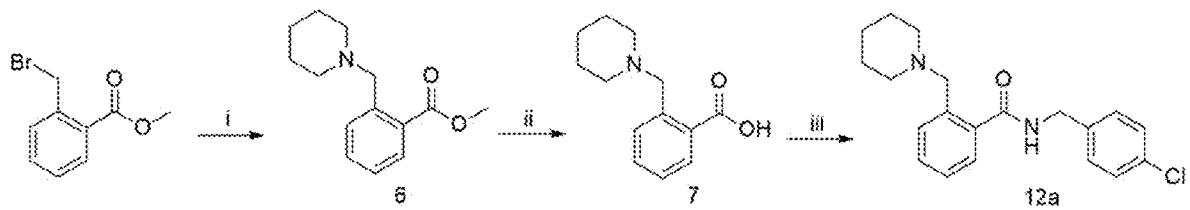

Synthetic routes for the preparation of various compounds tested herein are summarized in FIG. 1 (Schemes 1-3). The 2-/3-/4-(N-piperidinyl)methyl benzoic acid methyl esters 6, 4, and 2, were synthesized from the corresponding bromomethylbenzoic acid methyl ester and piperidine. After a subsequent hydrolysis step with sodium hydroxide, the (N-piperidinyl)methyl substituted esters were converted to the key acid intermediates 7, 5, and 3. Finally, condensation of these carboxylic acids with a series of substituted benzylamines or phenylethylamines resulted in the compounds, 11a-d, 12a-h, and 13a-d.

Figure 2:
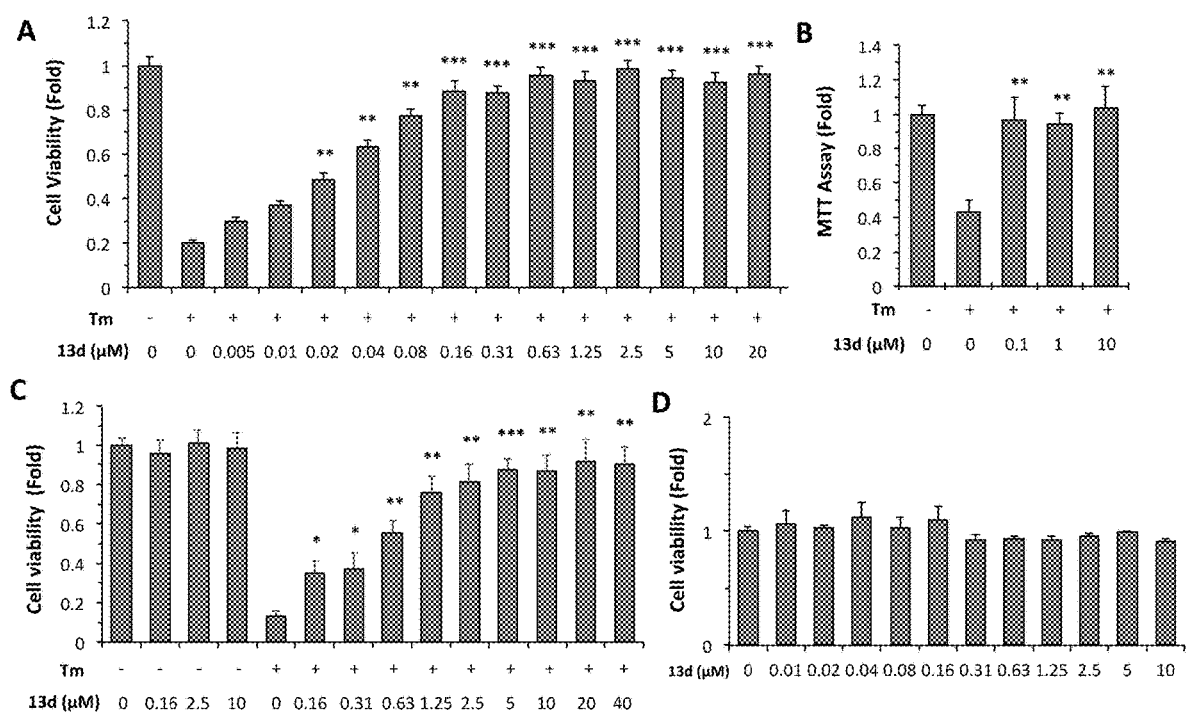
FIG. 2 shows how compound 13d protects the viability of INS-1 cells after Tm treatment. (A, B) INS-1 cells were treated with or without Tm (0.1 μg/mL) in the presence of 13d or DMSO for 72 h. Cell viability was determined by intracellular ATP assay (A) or MTT assay (B). (C) βTC6 cells were treated with or without Tm (0.3 μg/mL) in the presence of 13d or DMSO for 72 h. The cell viability was determined by the intracellular ATP level. (D) INS-1 cells were treated with 13d or DMSO for 72 h. The cell viability was determined by the intracellular ATP level. Results in A-C are expressed as the fold change compared with that of no Tm treatment (set to 1.0). The result in D is expressed as the fold-change compared to no 13d treatment (set to 1.0).

The measurement of intracellular ATP level was use as a surrogate assay for cell viability. Compound 13d rescued the viability of INS-1 β-cells under Tm treatment in a dose-dependent manner and that 13d retained maximum β-cell-protective activity within a wide range of concentrations from 0.16-20 µM (FIG. 2A). To confirm the authenticity of 13d's protective effect on β-cell viability (not simply an increase in ATP-specific measurement), we used the MTT assay, which measures the activity of NAD(P)H-dependent cellular oxidoreductase enzymes, as an orthogonal method to measure cell viability. As shown in FIG. 2B, Tm treatment reduced MTT reading in INS-1 cells compared to that of DMSO treatment, and co-treatment with 13d restored the viability of INS-1 cells. To determine whether the protective effect of 13d on β-cells is specific to INS-1 cells, another β-cell line, βTC6, was used. As expected, Tm induced a reduction in viability in βTC6 cells, and co-treatment with 13d rescued the viability of βTC6 cells in a dose-dependent manner, as assessed by the intracellular ATP level (FIG. 2C). In addition, compound 13d on its own had no effect on β-cell viability in both cell lines (FIG. 2C-D). Taken together, these results indicate that compound 13d protects β-cells against ER stress.

To determine whether the increase in β-cell viability following treatment with 13d is caused by a suppression of apoptotic cell death, several apoptosis-related makers were measured. First, levels of cleaved caspase-3 and cleaved PARP were assayed by Western blotting. Caspase-3, a member of executioner caspases activated by cleavage, plays essential roles in initiating apoptotic signaling and executing the final stages of cell death, whereas the nuclear enzyme poly (ADP-ribose) polymerase (PARP) plays an important role in a number of cellular processes involving DNA repair and cell death. Under normal condition, caspase 3 exists as inactive proenzyme. However, upon severe ER stress, caspase 3 undergoes proteolytic cleavage to produce two subunits that dimerize to form the active enzyme, which in turns cleaves PARP. Hence, appearance of the cleaved forms of both caspase-3 and PARP is an indication of apoptosis. Tm treatment for 24 h significantly induced both cleaved caspase-3 and cleaved PARP protein levels in INS-1 cells (FIG. 3A). However, 13d co-treatment completely or significantly diminished Tm-induced cleavage of both caspase-3 and PARP (FIG. 3A). Consistent with this, significantly more viable INS-1 cells were observed with Tm and 13d co-treatment than with Tm alone (FIG. 3B). A further assessment of apoptotic INS-1 cell death was performed using TUNEL assays to detect nuclear DNA fragmentation (a consequence of cell apoptosis) in situ. Tm treatment resulted in a significant increase in TUNEL-positive cells (7% TUNEL-positive cells compared to less than 0.2% in control group), while co-treatment with Tm and 13d remarkably reduced the TUNEL-positive cells (0.5%) (FIG. 3C-D). Taken together, these results demonstrate that 13d can suppress Tm-induced β-cell apoptosis.

In addition to β-cell apoptosis, ER stress also leads to β-cell dysfunction, namely, the impairment of biosynthesis and secretion of insulin. First, we examined whether compound 13d reverses the Tm-suppressed mRNA levels of insulin genes. As expected, Tm treatment of INS-1 cells decreased the mRNA levels of both insulin genes, INS1 and INS2, but this reduction was completely rescued by 13d (FIG. 4A-B). Second, we examined whether compound 13d affects the expression of β-cell transcription factors PDX1 and MafA, which control β-cell identity and the expression of insulin genes. Tm treatment decreased the levels of PDX1 and MafA mRNA expression levels in INS-1 cells, however, these decreases were completely rescued by 13d co-treatment (FIG. 4C-D). Next, we investigated whether compound 13d re-establishes Tm-impaired glucose-stimulated insulin secretion (GSIS). As shown in FIG. 4E, Tm treatment abolished the insulin secretion caused by high concentration of glucose treatment (20 mM) in INS-1 cells. Addition of 13d significantly rescued the GSIS in Tm-treated cells. Taken together, these data demonstrate that 13d restores ER stress-impaired β-cell survival and function.

Having established that compound 13d restores ER stress-impaired β-cell survival and function, we next investigated the mechanism of action by which 13d protects β-cells against ER stress. Chronic or severe ER stress activates all three branches of the UPR, PERK, IRE1α, and ATF6, leading to eventual cell death. First, we determined the effect of 13d on the activation of the PERK pathway in β-cells under ER stress. PERK activation phosphorylates eukaryotic translation initiator factor 2α (eIF2α), which in turn allows for the up-regulation of activating transcription factor 4 (ATF4) and of the pro-apoptotic gene C/EBP-homologous protein (CHOP). Thus, we used ATF4 and CHOP expression levels as markers of PERK pathway activation. Tm treatment of INS-1 cells significantly increased the mRNA levels of both ATF4 and CHOP, whereas co-treatment with 13d almost completely abolished the Tm-induced increase in both mRNA levels (FIG. 5A-B). In addition, after treatment with Tm for 8 h, CHOP mRNA level increased 7-fold compared with the control group, and co-treatment with compound 13d inhibited Tm-induced CHOP expression with an $IC_{50}$ value of 0.037 μM (FIG. 5C). Moreover, this $IC_{50}$ value was almost equal to the $EC_{50}$ value of 13d for cell survival (Table 5). In addition, 13d had no effect on the mRNA levels of ATF4 and CHOP on its own (FIG. 5D-E). These results indicate that 13d inhibits the activation of PERK-ATF4-CHOP pathway of the UPR under ER stress.

Next, we determined the effect of 13d on the activation of IRE1α in β-cells under ER stress. Activation of the IRE1α leads to cleavage of X-box binding protein-1 (XBP1) mRNA and this generates a spliced form (XBP1s) that is translated into a potent transcription factor that controls the expression of UPR genes involved in ER protein folding and degradation. We therefore used XBP1 splicing as a marker for the activation of the IRE1α pathway and determined the effect of 13d on IRE1α-mediated XBP1 splicing in INS-1 cells in the presence of Tm. As shown in FIG. 6A, Tm markedly increased the level of XBP1s mRNA in INS-1 cells, but this increase was abolished by 13d co-treatment, as measured by qRT-PCT using XBP1 splicing-specific primers. Similarly, an electrophoretic separation of spliced and unspliced forms of XBP1 after RT-PCR amplification of total XBP1 mRNA revealed that 13d inhibits the Tm-induced generation of XBP1s mRNA (FIG. 6B). These results indicate that 13d inhibits Tm-induced activation of IRE1α-XBP1 pathway.

We then investigated the effects of 13d on the activation of ATF6 in β-cells under ER stress. Activated ATF6 acts as a homodimer or as an ATF6-XBP1s heterodimer to control the up-regulation of select UPR target genes including the chaperone proteins BiP and GRP94. Therefore, these two chaperone proteins were evaluated in the INS-1 cells in the presence of Tm. Both Bip and GRP94 mRNAs were up-regulated by treatment with Tm, while co-treatment with Tm and compound 13d almost completely reversed these increases (FIG. 7A-B).

Thus far, our observation that 13d protected β-cells against ER stress-induced cell death and dysfunction and that 13d inhibited ER stress-mediated activation of all three UPR pathways revealed a strong correlation between the β-cell protective effect of 13d and its suppression of ER stress response. If 13d protects β-cells through the inhibition of ER stress response, a structurally similar but β-cell-inactive analog of 13d would be expected to possess no inhibitory effect on ER stress-induce UPR response. Indeed, we observed that as a negative control, the β-cell-inactive analog 8f had no effect on the UPR pathways. As shown in FIG. 8, 8f co-treatment had no obvious effect on the mRNA levels of ATF4, CHOP, Bip, GRP94 or XBP1s. These results together support the notion that 13d protects β-cell survival by alleviating ER stress.

We next evaluated the in vivo efficacy of 13d using a streptozotocin (STZ)-induced diabetic mouse model. STZ induces ER stress in β-cells in addition to the increase in reactive oxygen species (ROS) production and DNA alkylation. C57BL/6 mice injected intraperitoneally with low dose STZ (50 mg/kg) once daily for 5 consecutive days develop diabetes; blood glucose levels increased gradually within a week of STZ treatment. Co-treatment with 13d (5 mg/kg) lowered the glucose levels significantly in a time-dependent manner (314 mg/dL (13d) vs. 422 mg/dL (vehicle) after 3 weeks of treatment) (FIG. 9A). The intraperitoneal glucose tolerance testing on overnight fasted animals showed lower blood glucose levels at 15, and 30 min in mice co-treated with STZ and 13d, compared to vehicle-treated STZ group (FIG. 9B).

To evaluate whether 13d treatment influences the survival of β-cells in STZ animals, histology on pancreatic sections was analyzed. We observed that 13d-treated mice had more than double the total pancreatic islet β-cell area compared to vehicle-treated mice (67.4±5.9% for STZ+13d vs. 30.2±7.9% for STZ+saline, FIG. 9C-D). In addition, 13d had no obvious effect on the average number of α-cells between vehicle and 13d groups (FIG. 9C). These results indicate that 13d ameliorates STZ-induced diabetes in mice by preserving β-cell survival.

Certain 3-(N-piperidinyl) methyl benzamide derivatives have been identified to have potent activity against ER stress-induced β-cell death and dysfunction. In one non-limiting embodiment, the 3-(N-piperidinyl) methyl benzamide analog 13d has near 100% β-cell-protective activity and an an $EC_{50}$ value of ~30 nM against ER stress. Compound 13d significantly lowers blood glucose levels and increases β-cell survival in an STZ-induced diabetic mouse model. Further, 13d alleviates ER stress/UPR response by inhibiting Tm-induced up-regulation of all three branches of unfolded protein response (UPR) and apoptosis. Without wishing to be bound by theory, FIG. 10 shows a proposed model of signaling events leading to the protective effect of 13d in β-cells against ER stress-induced dysfunction and cell death. In this model compound 13d inhibits or mitigates against the activity of ATF6, IRE1α, and PERK causing downstream effects which reduce ER stress.

Methods

Chemistry

The reagents were purchased and used without further purification. $^1$H NMR and $^{13}$C NMR spectra were recorded on a Bruker AC300 or a Bruker AC400 NMR spectrometer with tetramethylsilane as an internal reference. ESI-MS spectra were obtained on a Krats MS 80 mass spectrometer. Column chromatography was performed on silica gel (200-300 mesh). The purity of synthesized final compounds was determined by HPLC. Compounds 1, 8a-h, 9a-f, and 10a-p were purchased from ChemBridge. The structures and purities were confirmed using NMR and HPLC. The purities of all these compounds are more than 95%.

General Procedure for Compounds 3, 5 and 7

After the bromomethylbenzoic acid methyl ester (1 mmol) was dissolved in 4 mL of THF, piperidine (119 μL, 1.2 mmol) and $K_2CO_3$ (276 mg, 2 mmol) were added to the solution. The mixed solution was stirred at room temperature until the reaction was completed. The solution was poured into water (10 mL) and extracted with ethyl acetate (10 mL×3). The combined organic layer was washed with brine, dried over anhydrous sodium sulfate, filtered, and concentrated to afford the desired (N-piperidinyl)methyl benzoic acid methyl esters 2, 4 and 6. The crude ester was added to a mixed solution of $H_2O$ (2 mL) and methanol (2 mL) with sodium hydroxide (60 mg, 1.5 mmol). The solution was stirred at room temperature overnight. After the methanol was evaporated under vacuum, the pH of the residue aqueous layer was adjusted to 5. The formed precipitate was filtered, washed with cold water, and dried under vacuum to afford the desired product. 4-(N-piperidinyl) methyl benzoic acid (3) was obtained as a white solid from 4-bromomethyl benzoic acid methyl ester in 65% yield. 3-(N-piperidinyl) methyl benzoic acid (5) was obtained as a white solid from 3-bromomethyl benzoic acid methyl ester in 59% yield. $^1$H NMR (400 MHz, DMSO-d6): δ 10.78 (s, 1H), 8.17 (s, 1H), 8.01 (m, 2H), 7.59 (m, 1H), 4.35 (s, 2H), 3.32 (m, 2H), 3.17 (m, 2H), 2.53 (s, 2H), 1.80 (m, 6H). 2-(N-piperidinyl)methyl benzoic acid (7) was obtained as a white solid from 2-bromomethyl benzoic acid methyl ester in 68% yield. $^1$H NMR (400 MHz, CDCl3): δ 8.18 (dd, 1H, J=6.0, 1.2 Hz), 7.46 (m, 1H), 7.40 (m, 1H), 7.15 (d, J=6.0 Hz), 3.84 (s, 2H), 3.15 (m, 2H), 2.36 (m, 2H), 1.82 (m, 2H), 1.60 (m, 4H).

General Procedure and Characterization of Compounds 11a-11d, 12a-12h, and 13a-13d To a solution of compound 3, 5 or 7 (1 mmol) in anhydrous dichloromethane (5 mL), corresponding benzylamines or phenylethylamines (1.2 mmol), HATU (1.5 mmol), and DIEA (2 mmol) were added. The mixed solution was stirred at room temperature. After the reaction was completed, $H_2O$ (5 mL) was added to the solution. The organic layer was separated and washed with brine, dried over anhydrous sodium sulfate, filtered, concentrated, and purified by flash column chromatography to afford the desired product.

11a was obtained as a solid from 3 and 4-chlorophenyl-ethylamine according to the general procedure in 61% yield. $^1$H NMR (400 MHz, DMSO-d6): δ 8.53 (s, 1H), 7.89 (m, 2H), 7.42 (m, 2H), 7.35 (m, 2H), 7.26 (m, 2H), 3.48 (m, 4H), 2.84 (m, 2H), 2.43 (m, 2H), 1.54-1.24 (m, 8H). $^{13}$C NMR (100 MHz, DMSO-d6): δ 166.41, 139.07, 131.20, 131.03, 128.69, 127.61, 52.83, 34.80. LC-MS (ESI+): 357 (M+H)$^+$.

11b was obtained as a solid from 3 and 3,4-dichlorophenylethylamine according to the general procedure in 81% yield. $^1$H NMR (400 MHz, DMSO-d6): δ 9.52 (br, 1H), 8.58 (m, 1H), 7.83 (m, 2H), 7.54 (m, 4H), 7.24 (m, 1H), 4.25 (s, 2H), 3.52 (m, 2H), 2.86 (m, 3H), 1.75-0.163 (m, 7H). $^{13}$C NMR (100 MHz, DMSO-d6): δ 141.36, 131.25, 131.22, 130.80, 129.73, 129.16, 127.78, 34.38. LC-MS (ESI+): 391 (M+H)$^+$.

11c was obtained as a solid from 3 and 4-chlorobenzylamine according to the general procedure in 78% yield. $^1$H NMR (400 MHz, DMSO-d6): δ 9.02 (br, 1H), 7.84 (m, 2H), 7.60 (m, 3H), 7.38 (m, 6H), 4.46 (s, 2H), 3.47 (m, 2H), 2.31 (m, 2H), 1.49-1.39 (m, 6H). $^{13}$C NMR (100 MHz, DMSO-d6): δ 166.61, 139.30, 131.72, 129.54, 129.03, 128.67, 127.62, 54.36, 42.44, 26.00, 23.89. LC-MS (ESI+): 343 (M+H)$^+$.

11d was obtained as a solid from 3 and 3,4-dichlorobenzylamine according to the general procedure in 63% yield. $^1$H NMR (400 MHz, DMSO-d6): δ 9.78 (br, 1H), 9.23 (m, 1H), 7.97 (m, 2H), 7.60 (m, 3H), 7.32 (m, 1H), 4.48 (s, 2H), 4.33 (s, 2H), 2.90 (s, 2H), 1.78-1.24 (br, 6H). $^{13}$C NMR (100 MHz, DMSO-d6): δ 166.18, 141.32, 131.70, 131.33, 130.97, 129.79, 129.74, 128.14, 52.40, 42.21, 22.88, 21.71. LC-MS (ESI+): 379 (M+H)$^+$.

12a was obtained as a solid from 7 and 4-chlorobenzylamine according to the general procedure in 78% yield. $^1$H NMR (400 MHz, DMSO-d6): δ 10.35 (br, 1H), 7.69 (m, 1H), 7.41-7.30 (m, 7H), 4.48 (d, 2H, J=6.4 Hz), 3.46 (s, 2H), 2.21 (m, 4H), 1.29 (m, 6H). $^{13}$C NMR (100 MHz, DMSO-d6): δ 168.30, 139.01, 137.29, 132.10, 132.03, 130.21, 129.96, 128.82, 128.06, 61.51, 53.32, 42.74, 40.67, 40.46, 40.25, 40.04, 39.83, 39.62, 25.74, 24.19. LC-MS (ESI+): 343 (M+H)$^+$.

12b was obtained as a solid from 5 and benzylamine according to the general procedure in 71% yield. $^1$H NMR (400 MHz, DMSO-d6): δ 9.15 (m, 1H), 7.99 (m, 2H), 7.63 (m, 1H), 7.56 (m, 1H), 7.47 (m, 1H), 7.38 (m, 1H), 7.30 (m, 2H), 4.56 (s, 2H), 4.16 (s, 2H), 2.93 (br, 4H), 1.67 (br, 4H), 1.48 (br, 2H). $^{13}$C NMR (100 MHz, DMSO-d6): δ 171.11, 144.77, 139.95, 133.85, 133.51, 132.50, 132.01, 58.72, 47.88, 28.12, 27.18. LC-MS (ESI+): 309 (M+H)$^+$.

12c was obtained as a solid from 5 and 2-chlorobenzylamine according to the general procedure in 66% yield. $^1$H NMR (400 MHz, DMSO-d6): δ 9.15 (m, 1H), 7.99 (m, 2H), 7.63 (m, 1H), 7.56 (m, 1H), 7.47 (m, 1H), 7.38 (m, 1H), 7.30 (m, 2H), 4.56 (s, 2H), 4.16 (s, 2H), 2.93 (br, 4H), 1.67 (br, 4H), 1.48 (br, 2H). $^{13}$C NMR (100 MHz, DMSO-d6): δ 166.06, 136.21, 134.48, 131.96, 130.51, 130.43, 129.51, 129.13, 128.68, 128.64, 128.59, 127.54, 127.14, 78.82, 78.69, 52.32, 51.73, 40.09, 22.13. LC-MS (ESI+): 343 (M+H)$^+$.

12d was obtained as a solid from 5 and 3-chlorobenzylamine according to the general procedure in 72% yield. $^1$H NMR (400 MHz, DMSO-d6): δ 10.10 (br, 1H), 9.32 (s, 1H), 8.00 (m, 2H), 7.68 (m, 1H), 7.57 (m, 1H), 7.37 (m, 4H), 4.51 (s, 2H), 4.35 (s, 2H), 3.32 (m, 2H), 2.89 (br, 4H), 1.68 (m, 5H), 1.35 (m, 1H). $^{13}$C NMR (100 MHz, DMSO-d6): δ 165.90, 142.11, 134.67, 134.10, 132.94, 130.53, 130.13, 130.02, 128.84, 127.11, 126.71, 125.98, 58.78, 51.78, 42.21, 22.31, 21.24. LC-MS (ESI+): 343 (M+H)$^+$.

12e was obtained as a solid from 5 and 4-chlorobenzylamine according to the general procedure in 75% yield. $^1$H NMR (400 MHz, DMSO-d6): δ 9.11 (m, 1H), 7.88 (m, 2H), 7.63 (m, 1H), 7.51 (m, 2H), 7.39 (m, 4H), 4.47 (m, 2H), 3.37 (m, 2H), 2.66 (m, 2H), 1.58 (m, 6H), 1.25 (m, 2H). $^{13}$C NMR (100 MHz, DMSO-d6): δ 166.54, 139.16, 134.87, 131.80, 129.63, 128.89, 128.70, 52.73, 42.54, 39.40, 23.51, 22.54. LC-MS (ESI+): 343 (M+H)$^+$.

12f was obtained as a solid from 3 and 2-chlorobenzylamine according to the general procedure in 72% yield. $^1$H NMR (400 MHz, DMSO-d6): δ 9.31 (br, 1H), 9.12 (m, 1H), 8.01 (m, 2H), 7.62 (m, 2H), 7.47 (m, 1H), 7.33 (m, 3H), 4.56 (m, 2H), 4,34 (s, 2H), 2.88 (m, 2H), 1.82 (m, 2H), 1.63 (m, 3H) 1.38 (m, 1H). $^{13}$C NMR (100 MHz, DMSO-d6): δ 166.24, 136.69, 132.50, 131.79, 129.66, 129.17, 129.13, 128.23, 127.64, 59.04, 52.46, 41.13, 22.86, 21.72. LC-MS (ESI+): 343 (M+H)$^+$.

12g was obtained as a solid from 3 and 3-chlorobenzylamine according to the general procedure in 81% yield. $^1$H NMR (400 MHz, DMSO-d6): δ 9.05 (m, 1H), 7.85 (m, 2H), 7.41-7.27 (m, 6H), 4.47 (m, 2H), 3.40 (m, 2H), 2.33 (m, 4H), 1.40 (m, 6H). $^{13}$C NMR (100 MHz, DMSO-d6): δ 166.62, 142.83, 133.41, 130.65, 127.67, 127.50, 127.15, 126.38, 54.29, 42.60. LC-MS (ESI+): 343 (M+H)$^+$.

12h was obtained as a solid from 3 and 3-bromobenzylamine according to the general procedure in 65% yield. $^1$H NMR (400 MHz, DMSO-d6): δ 9.04 (m, 1H), 7.84 (m, 2H), 7.50-7.29 (m, 6H), 4.46 (m, 2H), 3.46 (s, 2H), 2.31 (m, 4H), 1.50-1.38 (m, 6H). $^{13}$C NMR (100 MHz, DMSO-d6): δ 166.64, 143.13, 142.85, 133.16, 130.96, 130.41, 130.05, 129.02, 127.62, 126.79, 122.05, 62.88, 54.40, 42.55, 26.05, 24.44. LC-MS (ESI+): 389 (M+H)$^+$.

13a was obtained as a solid from 5 and 3-methoxybenzylamine according to the general procedure in 72% yield. $^1$H NMR (400 MHz, CDCl3): δ 7.78 (m, 1H), 7.74 (m, 1H), 7.46 (m, 1H), 7.38 (m, 1H), 7.29 (m, 1H), 6.97 (m, 1H), 6.92 (m, 1H), 6.84 (m, 1H), 6.65 (s, 1H), 4.62 (d, 2H, J=6.0 Hz), 3.81 (s, 3H), 3.60 (s, 2H), 3,49 (s, 2H), 2.49 (br, 4H), 1.55 (m, 3H), 1.37 (m, 1H). $^{13}$C NMR (100 MHz, DMSO-d6): δ 166.22, 159.24, 141.30, 134.20, 131.63, 129.30, 128.05, 127.70, 125.69, 119.37, 112.95, 111.97, 62.61, 54.91, 53.85, 42.53, 25.47, 23.93. LC-MS (ESI+): 339 (M+H)$^+$.

13b was obtained as a solid from 5 and 4-methoxybenzylamine according to the general procedure in 68% yield. $^1$H NMR (400 MHz, DMSO-d6): δ 9.27 (br, 1H), 9.07 (m, 1H), 8.03 (d, 1H, J=6.0 Hz), 7.97 (d, 1H, J=6.0 Hz), 7.64 (d, 1H, J=6.0 Hz), 7.58 (d, 1H, J=6.0 Hz), 7.26 (m, 2H), 6.90 (m, 2H), 4.43 (d, 2H, J=4.8 Hz), 4.33 (d, 2H, J=3.6 Hz),3.46 (s, 3H), 3.32 (m, 2H), 2.89 (m, 2H), 1.68 (m, 2H), 1.63 (m, 3H), 1.35 (m, 1H). $^{13}$C NMR (100 MHz, DMSO-d6): δ 165.55, 158.22, 134.98, 134.02, 131.41, 130.67, 129.93, 128.79, 128.67, 127.87, 113.67, 58.86, 55.05, 51.91, 42.13, 22.38, 21.24. LC-MS (ESI+): 339 (M+H)$^+$.

13c was obtained as a solid from 5 and 3-trifluoromethyl benzylamine according to the general procedure in 68% yield. $^1$H NMR (400 MHz, DMSO-d6): δ 9.13 (m, 1H), 7.79 (m, 2H), 7.66 (m, 4H), 7.44 (m, 2H), 4.56 (d, 2H, J=4.4 Hz), 3.46 (s, 2H), 2.31 (br, 4H), 1.49 (m, 4H), 1.37 (m, 2H). $^{13}$C NMR (100 MHz, DMSO-d6): δ 166.40, 141.23, 139.02, 133.96, 131.77, 131.45, 129.37, 128.13, 127.63, 125.70, 123.76, 123.73, 123.51, 123.48, 62.61, 53.88, 42.24, 25.50, 23.96. LC-MS (ESI+): 377 (M+H)$^+$.

13d was obtained as a solid from 5 and 4-trifluoromethyl benzylamine according to the general procedure in 74% yield. $^1$H NMR (400 MHz, DMSO-d6): δ 9.15 (m, 1H), 7.80 (m, 2H), 7.70 (m, 2H), 7.54 (m, 2H), 7.41 (m, 2H), 4.56 (s, 2H), 3.45 (s, 2H), 2.31 (br, 4H), 1.49 (m, 4H), 1.38 (m, 2H). $^{13}$C NMR (100 MHz, DMSO-d6): δ 166.35, 144.61, 139.00, 133.92, 131.78, 128.12, 127.87, 127.69, 125.73, 125.19, 125.17, 125.14, 125.10, 62.64, 53.89, 42.32, 35.49, 23.96. LC-MS (ESI+): 377 (M+H)$^+$.

Cell Culture

INS-1 cells were cultured in RPMI 1640 (Corning, N.Y., USA) supplemented with 10% FBS (Atlanta Biologicals, Norcross, Ga.), HEPES (10 mM, Life Technologies, CA, USA), sodium pyruvate (1 mM, Corning), 2-mercaptoethanol (50 μM, Sigma, St Louis, Mo., USA) and antibiotics (100 UI/mL penicillin and 100 μg/mL streptomycin, Corning). βTC6 cells were cultured in DMEM (Corning) with 15% FBS, sodium pyruvate (1 mM, Corning), non-essential amino acids (1 mM, Thermo, Ill., USA), GlutaMAX (1 mM, Life Technologies) and antibiotics (100 UI/mL penicillin and 100 μg/mL streptomycin). All cells were grown at 37° C. in a humidified 5% $CO_2$ atmosphere.

Cell Survival Assay

INS-1 cells or βTC6 cells were seeded at $3 \times 10^3$ cells/well in a 384-well plate and treated with compounds at the indicated concentrations. After 3 d treatment, the medium was aspirated and 20 μL/well of CellTiter-Glo reagent (Promega, WI, USA) was added for the detection of intracellular ATP levels. Cell viability was measured with an EnVision multilabel plate reader (PerkinElmer, MA, USA).

RNA Isolation, RT-PCR and qRT-PCR

INS-1 cells were seeded at $4 \times 10^5$ cells/well in 6-well plates and treated with compounds for the indicated times. Total RNA was extracted using TRIzol reagent (Invitrogen, Carlsbad, Calif.) according to the manufacturer's protocol, and 2 μg of total RNA was reverse transcribed using a Superscript kit (Invitrogen). Real-time PCR was performed in 96-well format using SYBR Select Master Mix (Applied Biosystems, Foster City, Calif.) with an ABI 7500 PCR system (Applied Biosystems). Relative mRNA levels were normalized against the housekeeping gene Cyclophilin A and were determined by ΔΔCt calculated from the difference in ΔCt values between the target gene and Cyclophilin A with and without treatment, based on comparative CT (cycle threshold) method. Comparisons were performed by two-tailed paired Student's t-test to obtain P values. The primer sequences used were:

```
Rat CHOP:
                                      (SEQ ID NO: 1)
forward (F), 5'-GAAATCGAGCGCCTGACCAG-3'
and (SEQ ID NO: 2)
reverse (R), 5'-GGAGGTGATGCCAACAGTTCA-3'.

Rat ATF4:
                                      (SEQ ID NO: 3)
F, 5'- TCCTGAACAGCGAAGTGTTG-3'
and (SEQ ID NO: 4)
R, 5'-GTGTCTGAGGCACTGACCAA-3'.

Rat Bip:
                                      (SEQ ID NO: 5)
F, 5'-CTATTCCTGCGTCGGTGTATT-3'
and (SEQ ID NO: 6)
R, 5'-GGTTGGACGTGAGTTGGTTCT-3'.

Rat GRP94:
                                      (SEQ ID NO: 7)
F, 5'- TCCCCCTTAATGTTTCCCGTG-3'
and (SEQ ID NO: 8)
R, 5'-TAGCCCTTCTTCAGAAGCCTC-3'.

Rat XBP1s:
                                      (SEQ ID NO: 9)
F, 5'- CTGAGTCCGAATCAGGTGCAG-3'
and (SEQ ID NO: 10)
R, 5'-ATCCATGGGAAGATGTTCTGG-3'.

Rat XBP1 for regular PCR (XBP1u and XBP1s):
                                      (SEQ ID NO: 11)
F, 5'-GCTTGTGATTGAGAACCAGG-3', (SEQ ID NO: 12)
R, 5'-GAAAGGGAGGCTGGTAAGGAAC-3'.

Rat Ins1:
                                      (SEQ ID NO: 13)
F, 5'- GTCCTCTGGGAGCCCAAG-3'
and (SEQ ID NO: 14)
R, 5'-ACAGAGCCTCCACCAGG-3'.

Rat Ins2:
                                      (SEQ ID NO: 15)
F, 5'- ATCCTCTGGGAGCCCCGC-3'
and (SEQ ID NO: 16)
R, 5'-AGAGAGCTTCCACCAAG-3'.

Rat PDX1:
                                      (SEQ ID NO: 17)
F, 5'-GAGGACCCGTACAGCCTACA-3'
and (SEQ ID NO: 18)
R, 5'-CGTTGTCCCGCTACTACGTT-3'.

Rat MafA:
                                      (SEQ ID NO: 19)
F, 5'- AGCGGTCATATTTTCGCAAC-3'
and (SEQ ID NO: 20)
R, 5'-CTCTACAGGGAGCAGCGAAC-3'.

Rat Cyclophilin A:
                                      (SEQ id NO: 21)
F, 5'-GGTGACTTCACACGCCATAA-3'
and (SEQ ID NO: 22)
R, 5'-CTTCCCAAAGACCACATGCT-3'.
```

Western Blotting

INS-1 cells were seeded in 60-mm dishes at $8 \times 10^5$ cells/dish and treated for the indicated times. Cells were then washed with PBS and lysed with lysis buffer (Cell Signaling Technology, Danvers, Mass.) containing EDTA (Thermo, Ill.) and phosphatase inhibitors (Thermo). Aliquots of 20 µg total protein were separated on 7% SDS-PAGE gels (Life Technologies) and transferred to PVDF membranes (Life Technologies). The membranes were probed with primary antibodies followed by the appropriate HRP-conjugated secondary antibodies (goat anti-rabbit IgG and goat anti-mouse IgG, 1:3000; Santa Cruz Biotechnology, CA, USA). Blots were then developed. The primary antibodies and dilutions used were: CHOP (1:1000, MA1-250, Thermo), ATF4 (1:1000, 10835-1-AP, ProteinTech Group, IL, USA), cleaved caspase 3 (1:1000, 9661, Cell Signaling Technology, MA, USA), PARP (1:1000, 9542L, Cell Signaling Technology), and α-tubulin (1:3000, SC-8035, Santa Cruz Biotechnology).

MTT Assay

INS-1 cells or βTC6 cells were seeded at $3 \times 10^3$ cells/well in a 384-well plate and treated with compounds at the indicated concentrations. After 3 d treatment, the medium was aspirated and 10 µl of MTT reagent (Cayman Chemical, MI, USA, prepared according to manufacturer's instruction) to each well was added and mixed gently for one minute on an orbital shaker. The cells were then incubated for three hours at 37° C. in a $CO_2$ incubator. After incubation, add 100 µl of crystal dissolving solution to each well, and incubate for 4 hours in a 37° C. $CO_2$ incubator. Viability will be measured for the absorbance to each sample at 570 nm using EnVision multilabel plate reader (PerkinElmer, MA, USA).

Glucose-Stimulated Insulin Secretion

INS-1 or primary human islet cells were plated in 96-well plates. The second day, Tm and test compound were added and maintained for 24 h (INS-1) or 48 h (human islets). Cells were then incubated in fresh KRBH buffer (115 mM NaCl, 5 mM KCl, 24 mM $NaHCO_3$, 2.5 mM $CaCl_2$, 1 mM $MgCl_2$, 10 mM HEPES, 2% w/v BSA, pH 7.4) containing 2.5 mM glucose for 1 h. Cells were incubated for an additional hour in KRBH buffer containing 2.5, 25 (for INS-1 cells), or 20 (for human islets) mM glucose. The secreted insulin was measured with insulin ELISA kits (for mouse insulin from Millipore and for human insulin from LifeTech). Cells were lysed with RIPA buffer (50 mM Tris HCl pH 7.4, 1% NP-40, 0.25% sodium deoxycholate, 150 mM NaCl), and total cellular protein was determined with a Bradford protein assay. The secreted insulin levels were corrected for total protein.

Immunofluorescent and TUNEL Staining

Primary human islets were washed with PBS and fixed with 4% paraformaldehyde for 30 min. Fixed cells were then blocked in 5% normal donkey serum for 30 min. Polyclonal guinea pig anti-insulin (A0564, Dako, 1:500 dilution) was used as primary antibody. Donkey Cy3 anti-guinea pig IgG was used as the secondary antibody. TUNEL staining was performed with In Situ Cell Death Detection Kit-Fluorescein (Roche) according to the manufacturer's instructions. DAPI was used for nuclear counter-staining. Images were taken with an Olympus FV1000 confocal microscope.

Animal Study

All procedures involving animals were performed in accordance with the protocol approved by the University of Oklahoma Health Science Center Institutional Animal Care and Use Committee (IACUC). C57BL/6 mice were obtained from The Jackson Laboratory (Bar Harbor, Me.) and maintained on a 12 h light (6:00 AM-6:00 PM)-12 h dark (6:00 PM-6:00 AM) cycle at an ambient temperature of 21° C. Mice were given free access to water and food. All experiments were performed with age-matched male mice. Compounds were dosed during light cycle. For streptozotocin (STZ)-induced diabetic model, ten-week-old C57BL/6 mice were injected intraperitoneally (i.p.) once daily for five days with STZ (dissolved in Na-Citrate Buffer; 50 mg/kg) and either 13d (5 mg/kg body weight; 2 mg/ml in 10% DMSO in saline buffer; n=7 mice) or vehicle (n=6 mice). Injections of vehicle or 13d alone were then continued for 2 more weeks. Every third day, animals were fasted for 5 h and blood was obtained by tail snip. Blood glucose levels were measured using a glucometer (Nova Statstrip Xpress; Data Science International, St. Paul, Minn.). At the end of the treatment period, mice were sacrificed and the pancreases were removed, fixed in formalin, and paraffin-embedded. Tissue blocks were serially sectioned at intervals of 100 μm and 6 sections were stained with an anti-insulin antibody (A0564, 1:500 dilution; Dako), anti-glucagon antibody (G2654, 1:500 dilution; Sigma), and DAPI (0.5 μg/ml). Insulin-positive cells were used to demarcate islets, and the total islet area was measured with an Olympus FV1000 confocal microscopy and quantified with Image-J histogram software.

Statistical Analysis

Data are presented as means±SD unless specified. Comparisons were performed by two-tailed paired Student's t-test. A P value of <0.05 was considered statistically significant.

In accordance with the foregoing, the present disclosure is directed, in at least some embodiments, to the following:

Clause 1. A compound having a formula as represented by chemical structure I:

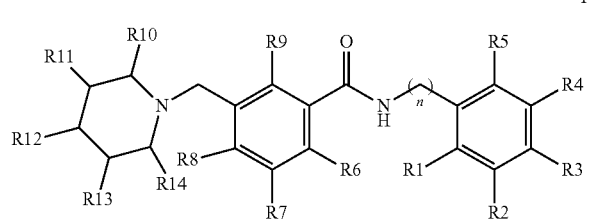

I wherein:
$R_1$-$R_{14}$ are independently selected from the group consisting of hydrogen (H), hydroxyl (OH), chlorine (Cl), fluorine (F), bromine (Br), iodine (I), alkyl, alkoxy, haloalkyl, and haloalkoxyl; and
n=1-10.

Clause 2. The compound of clause 1, wherein n is one or two.

Clause 3. The compound of clause 1, wherein at least one of $R_2$, $R_3$ and $R_4$ is an alkyl.

Clause 4. The compound of clause 1, wherein at least one of $R_2$, $R_3$ and $R_4$ is a methyl.

Clause 5. The compound of clause 1, wherein at least one of $R_2$, $R_3$ and $R_4$ is an ethyl.

Clause 6. The compound of clause 1, wherein at least one of $R_2$, $R_3$ and $R_4$ is an alkoxy.

Clause 7. The compound of clause 1, wherein at least one of $R_2$, $R_3$ and $R_4$ is a methoxy.

Clause 8. The compound of clause 1, wherein at least one of $R_2$, $R_3$ and $R_4$ is an ethoxy.

Clause 9. The compound of clause 1, wherein at least one of $R_2$, $R_3$ and $R_4$ is a haloalkyl.

Clause 10. The compound of clause 1, wherein at least one of $R_2$, $R_3$ and $R_4$ is a monohaloalkyl.

Clause 11. The compound of clause 1, wherein at least one of $R_2$, $R_3$ and $R_4$ is a dihaloalkyl.

Clause 12. The compound of clause 1, wherein at least one of $R_2$, $R_3$ and $R_4$ is a trihaloalkyl.

Clause 13. The compound of clause 1, wherein at least one of $R_2$, $R_3$ and $R_4$ is a haloalkoxyl.

Clause 14. The compound of clause 1, wherein at least one of $R_2$, $R_3$ and $R_4$ is a monohaloalkoxyl.

Clause 15. The compound of clause 1, wherein at least one of $R_2$, $R_3$ and $R_4$ is a dihaloalkoxyl.

Clause 16. The compound of clause 1, wherein at least one of $R_2$, $R_3$ and $R_4$ is a trihaloalkoxyl.

Clause 17. A composition comprising a pharmaceutically-acceptable carrier, diluent or vehicle, and the compound of any of clauses 1-16.

Clause 18. The composition of clause 17 further comprising one or more targeting molecules linked to the pharmaceutically acceptable carrier, vehicle, or diluent, or to the compound having chemical structure I, wherein the one or more targeting molecules are able to bind to a target cell or a portion of a target cell.

Clause 19. The composition of clause 18, wherein the target cell is a pancreatic β-cell.

Clause 20. A method of ameliorating a symptom associated with type 1 or type 2 diabetes in a subject in need of such therapy, comprising: administering to the subject an effective amount of the compound or composition of any one of clauses 1-19.

Clause 21. A use of the compound or composition of any one of clauses 1-19 for ameliorating a symptom associated with type 1 or type 2 diabetes in a subject, comprising administering to the subject an effective amount of said compound or composition.

Clause 22. A method of protecting pancreatic β cells from ER stress-induced dysfunction in a subject in need of such therapy, comprising: administering to the subject an effective amount of the compound or composition of any one of clauses 1-19.

Clause 23. A use of the compound or composition of any one of clauses 1-19 for protecting pancreatic β cells from ER stress-induced dysfunction in a subject, comprising administering to the subject an effective amount of said compound or composition.

It will be understood from the foregoing description that various modifications and changes may be made in the various embodiments of the present disclosure without departing from their true spirit. The description provided herein is intended for purposes of illustration only and is not intended to be construed in a limiting sense, except where specifically indicated. Thus, while the present disclosure has been described herein in connection with certain embodiments so that aspects thereof may be more fully understood and appreciated, it is not intended that the present disclosure be limited to these particular embodiments. On the contrary, it is intended that all alternatives, modifications and equivalents are included within the scope of the present disclosure as defined herein. Thus the examples described above, which include particular embodiments, will serve to illustrate the practice of the present disclosure, it being understood that the particulars shown are by way of example and for purposes of illustrative discussion of particular embodiments only and are presented in the cause of providing what is believed to be a useful and readily understood description of procedures as well as of the principles and conceptual aspects of the inventive concepts. Changes may be made in the formulation of the various compounds and compositions described herein, the methods described herein or in the steps or the sequence of steps of the methods described herein without departing from the spirit and scope of the present disclosure. All patents, published patent applications, and non-patent publications referenced in any portion of this application are herein expressly incorporated by reference in their entirety to the same extent as if each individual patent or publication was specifically and individually indicated to be incorporated by reference.

What is claimed is:

1. A compound consisting of a formula as represented by chemical structure I:

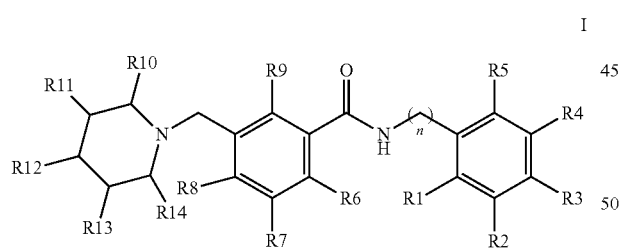

wherein:

$R_1$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_2$ is selected from the group consisting of hydrogen (H), hydroxyl (OH), chlorine (Cl), fluorine (F), bromine (Br), iodine (I), alkyl, haloalkyl, and haloalkoxyl;

$R_3$ is selected from the group consisting of hydrogen (H), hydroxyl (OH), chlorine (Cl), fluorine (F), bromine (Br), iodine (I), alkyl, haloalkyl, and haloalkoxyl;

$R_4$ is selected from the group consisting of hydrogen (H), hydroxyl (OH), chlorine (Cl), fluorine (F), bromine (Br), iodine (I), alkyl, haloalkyl, and haloalkoxyl;

$R_5$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_6$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_7$ is elected from the group consisting of hydrogen (H), hydroxyl (OH), chlorine (Cl), fluorine (F), bromine (Br), iodine (I), alkyl, alkoxy, haloalkyl, and haloalkoxyl;

$R_8$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_9$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{10}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{11}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{12}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{13}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{14}$ is selected from the group consisting of hydrogen (H), hydroxyl (OH), chlorine (Cl), fluorine (F), bromine (Br), iodine (I), alkyl, alkoxy, haloalkyl, and haloalkoxyl; and n=1-10, and wherein the compound is optionally linked to a targeting molecule selected from the group consisting of an antibody, an antibody fragment, a chimeric antibody, a monoclonal antibody, a peptide, a protein, an RNA, and a DNA, and wherein the targeting molecule is able to bind to a target cell or a portion of a target cell.

2. The compound of claim 1, wherein n is one or two.

3. The compound of claim 1, wherein at least one of $R_2$, $R_3$ and $R_4$ is an alkyl.

4. The compound of claim 1, wherein at least one of $R_2$, $R_3$ and $R_4$ is a methyl.

5. The compound of claim 1, wherein at least one of $R_2$, $R_3$ and $R_4$ is an ethyl.

6. The compound of claim 1, wherein at least one of $R_2$, $R_3$ and $R_4$ is a haloalkyl.

7. The compound of claim 1, wherein at least one of $R_2$, $R_3$ and $R_4$ is a monohaloalkyl.

8. The compound of claim 1, wherein at least one of $R_2$, $R_3$ and $R_4$ is a dihaloalkyl.

9. The compound of claim 1, wherein at least one of $R_2$, $R_3$ and $R_4$ is a trihaloalkyl.

10. The compound of claim 1, wherein at least one of $R_2$, $R_3$ and $R_4$ is a haloalkoxyl.

11. The compound of claim 1, wherein at least one of $R_2$, $R_3$ and $R_4$ is a monohaloalkoxyl.

12. The compound of claim 1, wherein at least one of $R_2$, $R_3$ and $R_4$ is a dihaloalkoxyl.

13. The compound of claim 1, wherein at least one of $R_2$, $R_3$ and $R_4$ is a trihaloalkoxyl.

14. A composition comprising the compound of claim 1 disposed in a pharmaceutically-acceptable carrier, diluent or vehicle.

15. The compound of claim 1, wherein the target cell is a pancreatic β-cell.

16. A method of ameliorating a symptom associated with type 1 or type 2 diabetes in a subject in need of such therapy, comprising:

administering to the subject an effective amount of the compound of claim 1.

17. A method of protecting pancreatic β cells from ER stress-induced dysfunction in a subject in need of such therapy, comprising:

administering to the subject an effective amount of the compound of claim 1.

18. The compound of claim 9, wherein the trihaloalky is $CF_3$.

19. The compound of claim 9, wherein $R_1$ and $R_5$-$R_{14}$=H, $R_2$-$R_4$ are independently selected from H and $CF_3$, and at least one of one of $R_2$, $R_3$, and $R_4$ is $CF_3$.

20. A compound consisting of Formula I:

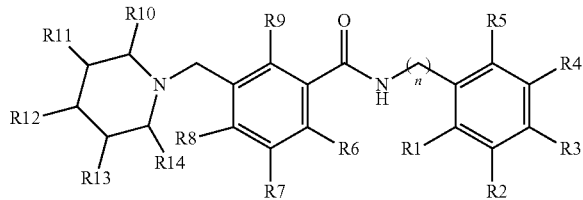

I wherein:

$R_1$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_2$ is selected from the group consisting of hydrogen (H) and trihaloalkyl;

$R_3$ is selected from the group consisting of hydrogen (H) and trihaloalkyl;

$R_4$ is selected from the group consisting of hydrogen (H) and trihaloalkyl;

$R_5$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_6$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_7$ is elected from the group consisting of hydrogen (H), hydroxyl (OH), chlorine (Cl), fluorine (F), bromine (Br), iodine (I), alkyl, alkoxy, haloalkyl, and haloalkoxyl;

$R_8$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_9$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{10}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{11}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{12}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{13}$ is selected from the group consisting of hydrogen (H), hydroxyl (OH), chlorine (Cl), fluorine (F), bromine (Br), iodine (I), alkyl, alkoxy, haloalkyl, and haloalkoxyl;

$R_{14}$ is selected from the group consisting of hydrogen (H), hydroxyl (OH), chlorine (Cl), fluorine (F), bromine (Br), iodine (I), alkyl, alkoxy, haloalkyl, and haloalkoxyl; and n=1-10, and with the proviso that at least one of $R_2$, $R_3$ and $R_4$ is a trihaloalkyl, and wherein the compound is optionally linked to a targeting molecule selected from the group consisting of an antibody, an antibody fragment, a chimeric antibody, a monoclonal antibody, a peptide, a protein, an RNA, and a DNA, and wherein the targeting molecule is able to bind to a target cell or a portion of a target cell.

21. The compound of claim 20, wherein n is one or two.

22. A composition comprising the compound of claim 20 and a pharmaceutically-acceptable carrier, diluent or vehicle.

23. The composition of claim 22 further comprising one or more targeting molecules linked to the pharmaceutically acceptable carrier, vehicle, or diluent, wherein the one or more targeting molecules are able to bind to a target cell or a portion of a target cell, and wherein the targeting molecule is selected from the group consisting of an antibody, an antibody fragment, a chimeric antibody, a monoclonal antibody, a peptide, a protein, an RNA, and a DNA.

24. The composition of claim 23, wherein the target cell is a pancreatic β-cell.

25. A method of ameliorating a symptom associated with type 1 or type 2 diabetes in a subject in need of such therapy, comprising: administering to the subject an effective amount of the compound of claim 20.

26. A method of protecting pancreatic β cells from ER stress-induced dysfunction in a subject in need of such therapy, comprising: administering to the subject an effective amount of the compound of claim 20.

27. The compound of claim 20, wherein the target cell is a pancreatic β-cell.

* * * * *